(12) United States Patent
Karasic et al.

(10) Patent No.: US 10,568,641 B1
(45) Date of Patent: Feb. 25, 2020

(54) RETRO GUIDEWIRE REAMER

(71) Applicants: Smith & Nephew, Inc., Memphis, TN (US); Smith & Nephew Pte. Limited, Singapore (SG); Smith & Nephew Orthopaedics AG, Baar (CH)

(72) Inventors: Geoffrey Karasic, Milton, MA (US); Miles Steven Holt Malone, Brighton, MA (US); Roman Gutierrez, Brighton, MA (US); David Callaghan, Hopkinton, MA (US); Matthew Cunningham, Lakeville, MA (US); Chun Liu, Brookline, MA (US)

(73) Assignee: Smith & Nephew, Inc., Memphis, TN (US)

(*) Notice: Subject to any disclaimer, the term of this patent is extended or adjusted under 35 U.S.C. 154(b) by 19 days.

(21) Appl. No.: 16/124,307

(22) Filed: Sep. 7, 2018

(51) Int. Cl.
*A61B 17/16* (2006.01)
*A61B 17/32* (2006.01)
*A61B 17/17* (2006.01)

(52) U.S. Cl.
CPC ...... *A61B 17/1617* (2013.01); *A61B 17/1615* (2013.01); *A61B 17/1622* (2013.01); *A61B 17/32002* (2013.01); *A61B 17/1633* (2013.01); *A61B 17/1714* (2013.01); *A61B 2017/320056* (2013.01)

(58) Field of Classification Search
CPC . A61B 17/16; A61B 17/1613; A61B 17/1615; A61B 17/1617; A61B 17/1633; A61B 17/1637; A61B 17/32002; A61B 2017/320056
See application file for complete search history.

(56) References Cited

U.S. PATENT DOCUMENTS 8,303,593 B2 * 11/2012 Simon ............... A61B 17/1615
606/180
2014/0276844 A1 * 9/2014 Bourque ............ A61B 17/1714
606/80

* cited by examiner

*Primary Examiner* — Larry E Waggle, Jr.
(74) *Attorney, Agent, or Firm* — Burns & Levinson, LLP; Joseph M. Maraia

(57) ABSTRACT

Retro guidewire reamers include a drill having a tubular shaft configured to be disposed over a guidewire and at least one cutting member movably disposed adjacent the distal end of the shaft. A slide actuator is moveably coupled to the shaft and to an actuator wire slidable along the shaft. The actuator wire is operative to move the at least one cutting member between a closed position and a deployed position when the slide actuator is moved along the shaft. The retro guidewire reamers include mechanisms to protect the mechanical joint between the actuator wire and the slide actuator which prevent the actuator wire from disengaging from the slide actuator when the cutting member is obstructed by a guidewire.

16 Claims, 19 Drawing Sheets

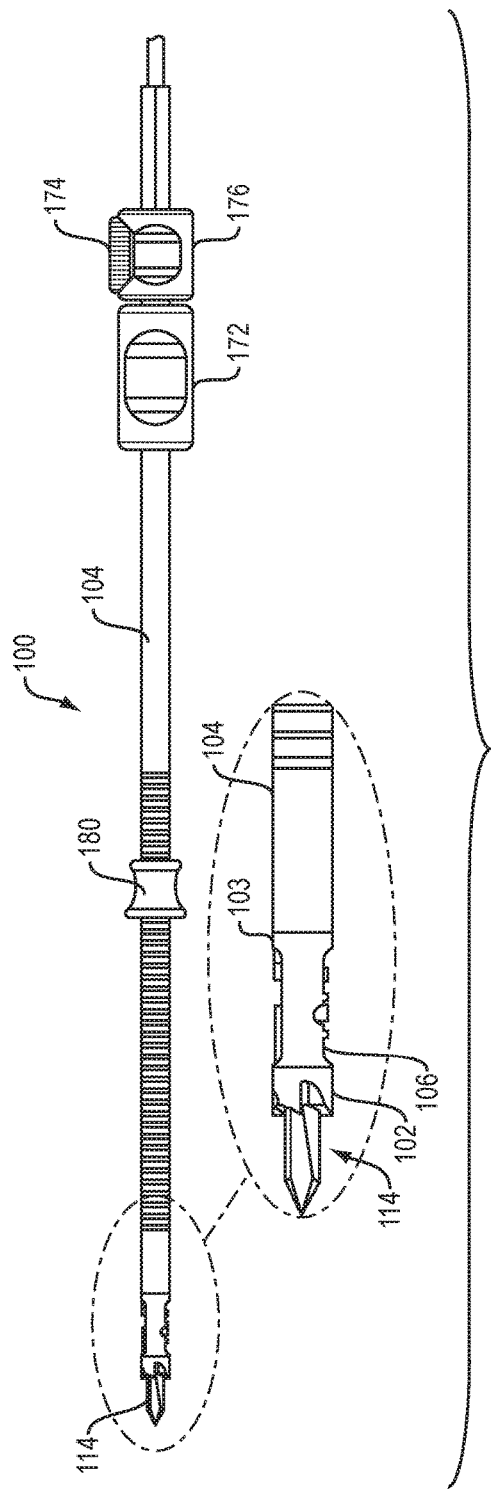
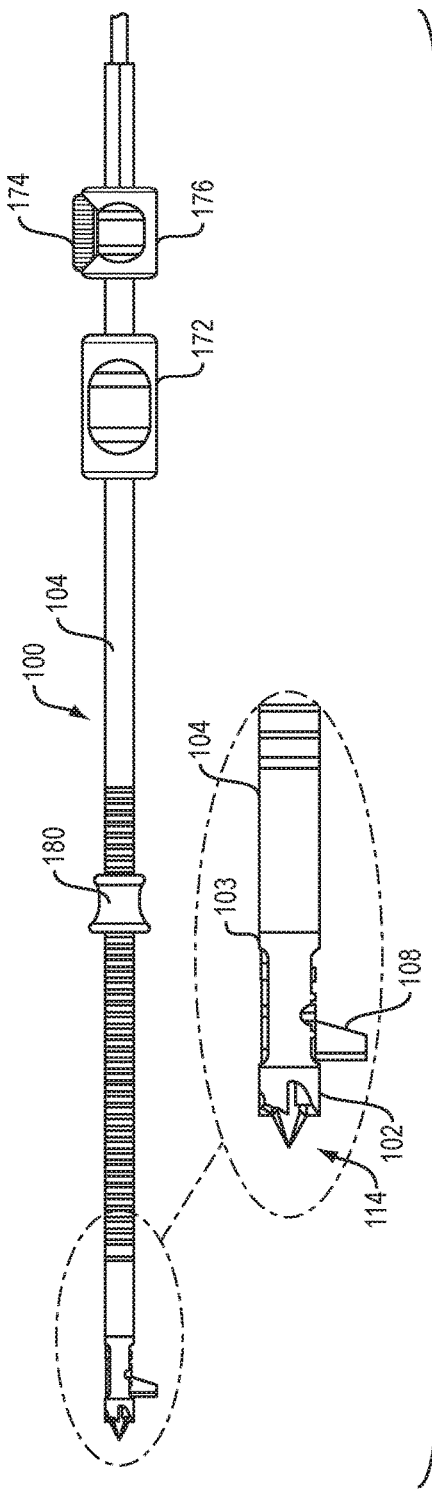
FIG. 1a (PRIOR ART)
FIG. 1b (PRIOR ART)

RETRO GUIDEWIRE REAMER

TECHNICAL FIELD

The present disclosure relates generally to surgical instruments and, more specifically, to surgical instruments for creating tunnels through bone during arthroscopic ligament reconstruction surgery.

BACKGROUND

Desired outcomes for arthroscopic ligament reconstruction surgery are generally achieved by establishing the proper shape and placement of torn tissue. While performing such surgery, a surgeon typically makes a small incision in a patient's skin covering the surgical site (e.g., a bone joint) to allow a surgical instrument to be placed in the bone joint and manipulated through arthroscopic visualization. One such instrument, sometimes known as a retro guidewire reamer, can be configured to operate in both an antegrade drilling mode and a retrograde cutting mode. The reamer is used to create tunnels through the patient's bone which are subsequently filled with a tissue graft, replicating the original damaged tissue.

For a torn anterior cruciate ligament (ACL) reconstruction, for example, one approach to achieving proper placement of the tissue graft includes creating a tunnel from the outside to the inside (i.e., from the "outside in") of the patient's femur. With this approach, a surgeon places a guidewire through bone along an established path for creation of the bone tunnel. The surgeon then determines the size of a primary bone tunnel as well as the size of a counterbore through the bone appropriate to fit the replacement tendon graft. Once the proper size of the bone tunnel is established, the surgeon places the reamer with an appropriately sized drill bit over the guidewire to create the primary bone tunnel in an antegrade manner. The surgeon then retracts the guidewire and activates a mechanism to open or deploy a cutting member of the retro guidewire reamer within the bone joint. The surgeon then uses the cutting member to create a counterbore through the bone in a retrograde manner. Once the counterbore is drilled, the surgeon activates the mechanism to close the cutting member, allowing the reamer to be withdrawn through the primary bone tunnel created by the drill bit.

In some instances, device failure can occur when the surgeon attempts to deploy the cutting member before the guidewire is fully retracted from the device. A similar error can occur when the surgeon attempts to rotate the cutting member back to its original position while the guidewire is still engaged with the cutting member. These errors can potentially cause damage to the mechanical joint which allows the cutting member to deploy and retract, rendering the device inoperable and requiring a replacement device.

SUMMARY

Described herein are retro guidewire reamers including a drill having a tubular shaft configured to be disposed over a guidewire and at least one cutting member movably disposed adjacent the distal end of the shaft. A slide actuator is moveably coupled to the shaft and to an actuator wire slidable along the shaft. The actuator wire is operative to move the at least one cutting member between a closed position and a deployed position when the slide actuator is moved along the shaft. The retro guidewire reamers of this disclosure advantageously include mechanisms to protect the mechanical joint between the actuator wire and the slide actuator which prevent the actuator wire from disengaging from the slide actuator when the cutting member is obstructed by a guidewire. Because of the mechanisms, the surgeon would see that motion of the slide actuator does not result in deployment of the cutting member and would recognize that the guidewire is obstructing the movement of the cutting member.

Examples of the retro guidewire reamer of this disclosure may include one or more of the following, in any suitable combination.

In examples, the retro guidewire reamer of this disclosure includes a tubular shaft having a distal end and a proximal end and configured to be disposed over a guidewire. At least one cutting member is movably disposed adjacent the distal end of the shaft and a slide actuator moveably coupled to the shaft. An actuator wire is slidable along the shaft. The actuator wire has a first end coupled to the slide actuator and a second end coupled to the at least one cutting member. The actuator wire is operative to move the at least one cutting member between a closed position and a deployed position when the slide actuator is moved along the shaft. One of the actuator wire and the slide actuator includes a plurality of teeth configured to engage a flexible member extending from the other of the actuator wire and the slide actuator. The flexible member is configured to allow for movement of the slide actuator relative to the shaft at a preselected force when the actuator wire is prevented from sliding along the shaft. In examples, the preselected force is between about 1 lbf and about 8 lbf. In further examples, the plurality of teeth are formed integrally with the one of the actuator wire and the slide actuator. In other examples, the plurality of teeth are formed separately and bonded to the one of the actuator wire and the slide actuator.

In other examples, the retro guidewire reamer of this disclosure includes a tubular shaft having a distal end and a proximal end and configured to be disposed over a guidewire. At least one cutting member is movably disposed adjacent the distal end of the shaft and a slide actuator is moveably coupled to the shaft. An actuator wire is slidable along the shaft. The actuator wire has a first end disposed within the slide actuator and a second end coupled to the at least one cutting member. The actuator wire is operative to move the at least one cutting member between a closed position and a deployed position when the slide actuator is moved along the shaft. A spring mechanism including a rod is fixedly disposed within the slide actuator and a shuttle member is configured to move along the rod adjacent at least one compression element. The shuttle member is coupled to the first end of the actuator wire and configured to compress the at least one compression element, allowing for movement of the slide actuator relative to the shaft when the actuator wire is prevented from sliding along the shaft. In examples, the at least one compression element is two compression elements, and the shuttle member is disposed between the two compression elements. In further examples, the at least one compression element is a spring. In other examples, the first end of the actuator wire is rigidly coupled to the shuttle member.

In further examples, the retro guidewire reamer of this disclosure includes a tubular shaft having a cannulation extending from a distal end to a proximal end and configured to be disposed over a guide wire. At least one cutting member is moveably disposed adjacent the distal end of the shaft. A sheath member is axially aligned with the shaft. The sheath member includes a pin having an outer portion projecting radially from the sheath member and an inner portion extending through a transverse hole in the shaft in communication with the cannulation. A slide actuator is moveably coupled to the shaft and operatively coupled to the at least one cutting member for moving the at least one cutting member between a retracted and a deployed position. The slide actuator includes an internal slot configured to receive the outer portion of the pin such that the outer portion of the pin is slideable within the slot, and at least one opening in communication with the slot. The at least one opening is configured to receive the outer portion of the pin. When the outer portion of the pin is not engaged with the at least one opening, the slide actuator is moveable relative to the shaft, and when the outer portion is engaged with the at least one opening, the slide actuator is fixed relative to the shaft. In examples, the at least one opening in the slide actuator is two openings corresponding to the retracted and deployed position of the cutting member, respectively. In other examples, the pin is attached to a spring element of the sheath. The spring element controls a displacement path of the pin. In further examples, the spring element is a beam spring.

In yet further examples, the retro guidewire reamer of this disclosure includes a tubular shaft having a cannulation extending from a proximal end to a distal end, and at least one cutting member moveably disposed adjacent the distal end of the shaft. A slot extends through a surface of the shaft in communication with the cannulation. A diameter of a proximal region and a distal region of the slot is selected to be wider than a diameter of an intermediate region of the slot. A slide actuator is slideably coupled to the shaft and operative to move the at least one cutting member between a retracted and a deployed position. The slide actuator includes a transverse opening in communication with the slot. The reamer also includes a pin having an outer portion and an inner portion terminating in a foot portion. A diameter of the foot portion is selected to be wider than a diameter of the inner portion. The pin is at least partially disposed within the opening of the slide actuator such that the foot portion extends into one of the proximal or distal regions of the slot. The pin is actuable from a first position, in which interference between the foot portion of the pin and the intermediate region of the slot prevents the slide actuator from axial movement along the shaft, to a second position, in which the foot portion of the pin extends into the cannulation of the shaft and the slide actuator is axially moveable along the shaft. In examples, a spring is radially disposed about the inner portion of the pin and configured to bias the outer portion of the pin away from the shaft. In examples, the inner portion of the pin is configured to axially slide along the intermediate portion of the slot. In other examples, the proximal and distal portions of the slot correspond to the retracted and deployed positions of the cutting member, respectively.

In other examples, the retro guidewire reamer of this disclosure includes a tubular shaft having a distal end, a proximal end, and a longitudinal axis extending therebetween. The distal end of the shaft defines a drilling tip. A cutting member is disposed within a cavity formed adjacent the distal end of the shaft. The cutting member has a first end pivotally attached to the shaft at a distal end of the cavity and a second end defining a cutting end. The cutting member is pivotable about an axis of rotation that is perpendicular to the longitudinal axis. An actuator wire extends along a groove in the shaft and is coupled to the first end of the cutting member. A slide actuator is operatively coupled to the actuator wire such that longitudinal movement of the slide actuator along the shaft is effective to pivot the cutting member about the axis of rotation between a retracted position, in which the cutting end does not protrude from the cavity, and a deployed position, in which the cutting end protrudes from the cavity. The deployed position of the cutting end is distal to the retracted position of the cutting end. In examples, the cavity includes holes on opposing sides of the shaft configured for the passage of pivot pins attached to the cutting member. In other examples, a pivot direction of the cutting member between the retracted and deployed positions is away from a user. In further examples, in the deployed position, the first end of the cutting member rests against a distal wall of the cavity such that the distal wall provides resistance to the cutting member during retrograde drilling.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The disclosure will be more fully understood by reference to the detailed description, in conjunction with the following figures, wherein:

FIGS. 1a-2b depict an example of a prior art retro guidewire reamer;

FIGS. 5b-e illustrate the use of the retro guidewire reamer of FIG. 5a;

DETAILED DESCRIPTION

Figure 2A:
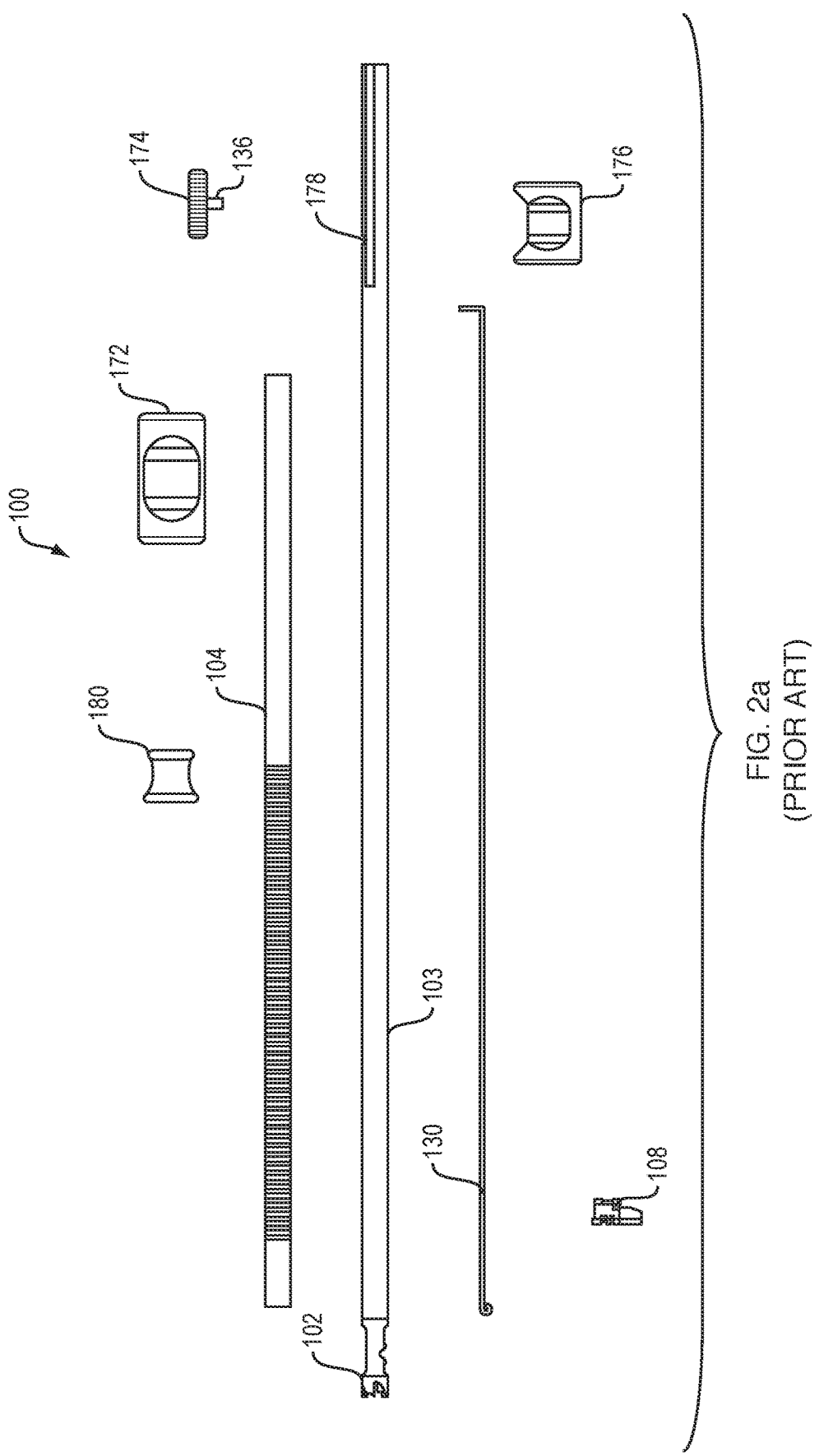

In the description that follows, like components have been given the same reference numerals, regardless of whether they are shown in different examples. To illustrate example(s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and claims, for the purposes of describing and defining the invention, the terms "about" and "substantially" are used to represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue. "Comprise," "include," and/or plural forms of each are open ended and include the listed parts and can include additional parts that are not listed. "And/or" is open-ended and includes one or more of the listed parts and combinations of the listed parts.

For a better understanding of the retro guidewire reamer of this disclosure, FIGS. 1a-2c show an example of prior art retro guidewire reamer 100 for securing a tissue to bone. FIG. 1a depicts a side view of the retro guidewire reamer 100, as well as a detailed view of a drill bit 102 having a tubular (cannulated) shaft 103 disposed over a guidewire 114. FIG. 1b depicts a further side view of the retro guidewire reamer 100, as well as a detailed view of the drill bit 102 and the cutting member 108 in its fully-opened or deployed position. As shown in FIGS. 1a and 1b, the shaft 103 extends through a sheath 104 with the cutting member 108 being operatively coupled within an opening or cavity 106 near a distal end of the shaft 103. The shaft 103 is coupled to a mechanism including, for example, a slide actuator 172, a lock knob 174, a plunger support 176, and a depth slide 180, for manually opening or deploying the cutting member 108, as further described below. The cutting member 108 can further include at least one through hole (not shown) allowing for the passage of the guidewire 114 through the cutting member 108 in its closed and/or open positions. In examples, the guidewire could be a 2.4 mm guidewire, or any other suitable guidewire or guide pin, designed to provide more accurate bone tunnel placement during arthroscopic ligament reconstruction surgery.

Figure 2B:
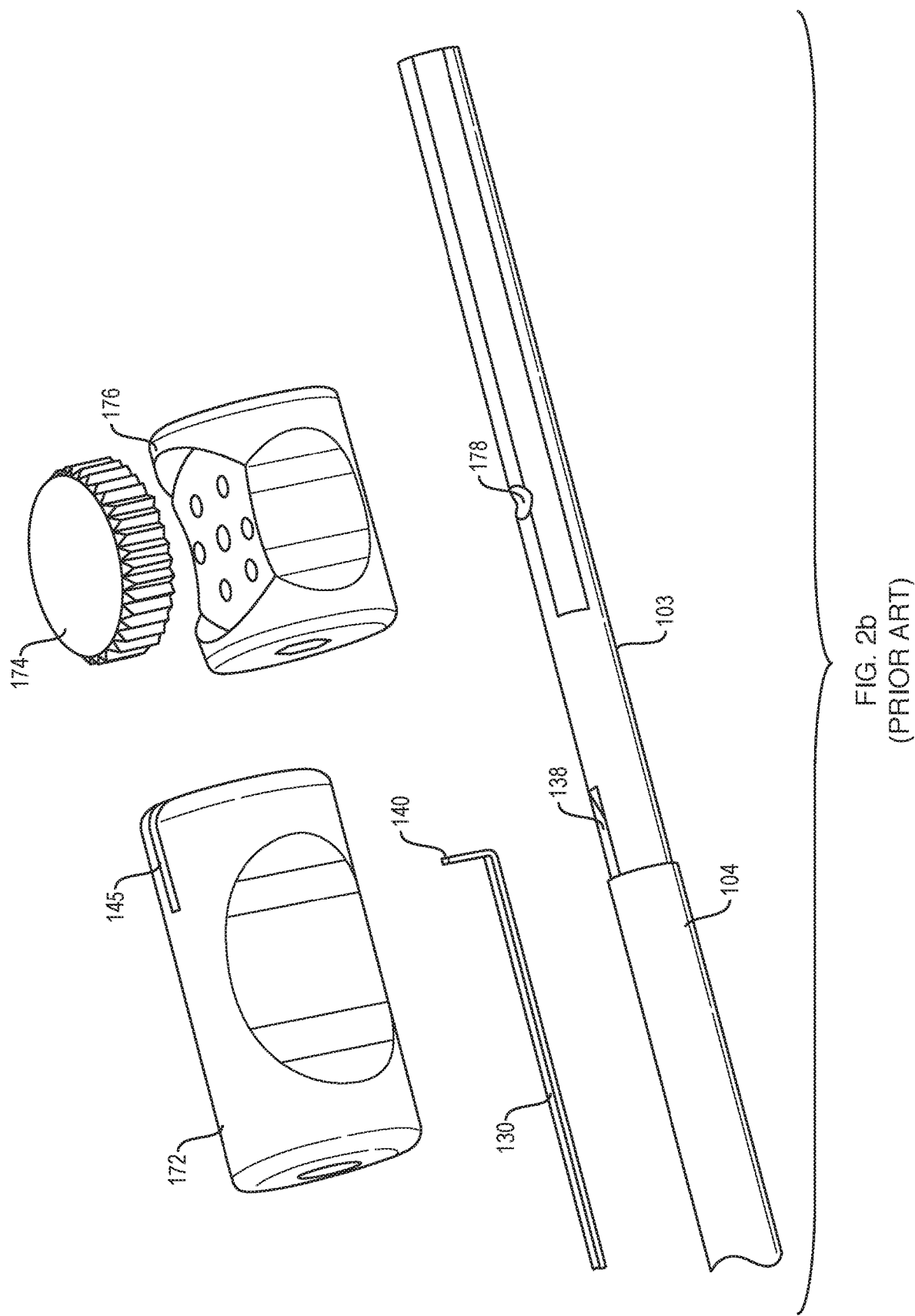

FIGS. 2a and 2b depict various components of the retro guidewire reamer 100, including the drill bit 102, the shaft 103, the sheath 104, the slide actuator 172, the lock knob 174, the plunger support 176, and the depth slide 180. The depth slide 180 can be used to determine the desired length of the counterbore formed by the cutting member 108. FIGS. 2a and 2b further include an actuator wire 130 connectable between the cutting member 108 and the slide actuator 172. The lock knob 174 can have a pin 136 configured to engage a hole 178 in the shaft 103, and to make contact with a guidewire disposed in the shaft 103. The shaft 103 can furthermore have a groove or slot 138 (FIG. 2b) extending along a surface for slidably accommodating the actuator wire 130. A projection 140 at the proximal end of the actuator wire 130 is configured to slide into a slot hole 145 formed in the slide actuator 172, forming a mechanical joint. During use, the mechanical joint allows the slide actuator 172 and the actuator wire 130 to cooperate to move the cutting member 108 from a closed position to its opened or deployed position, and vice versa. Further, during use, the lock knob 174 and the plunger support 176 cooperate to secure the guidewire within the shaft 103. The plunger support 176 also acts to limit proximal travel of the slide actuator 172.

Figure 3A:
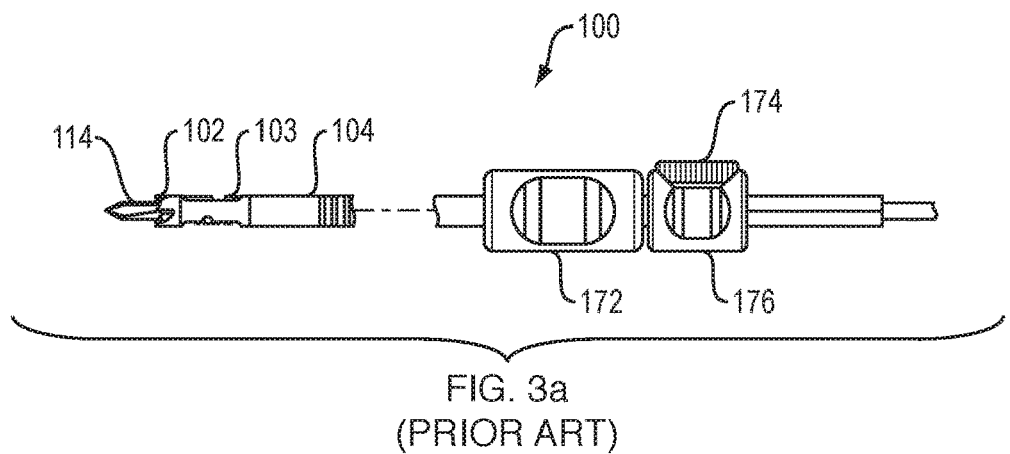
FIGS. 3a-c illustrate the use of the retro guidewire reamer of FIGS. 1a-2c.
Figure 3B:
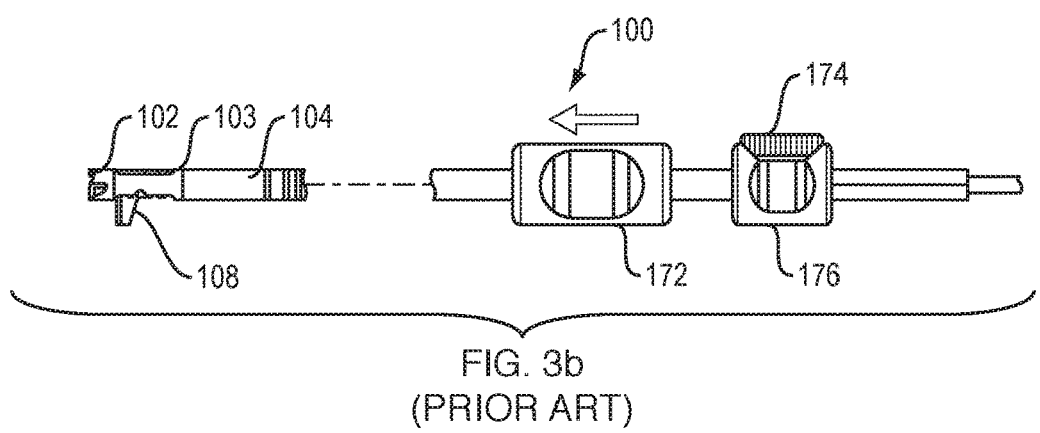
Figure 3C:
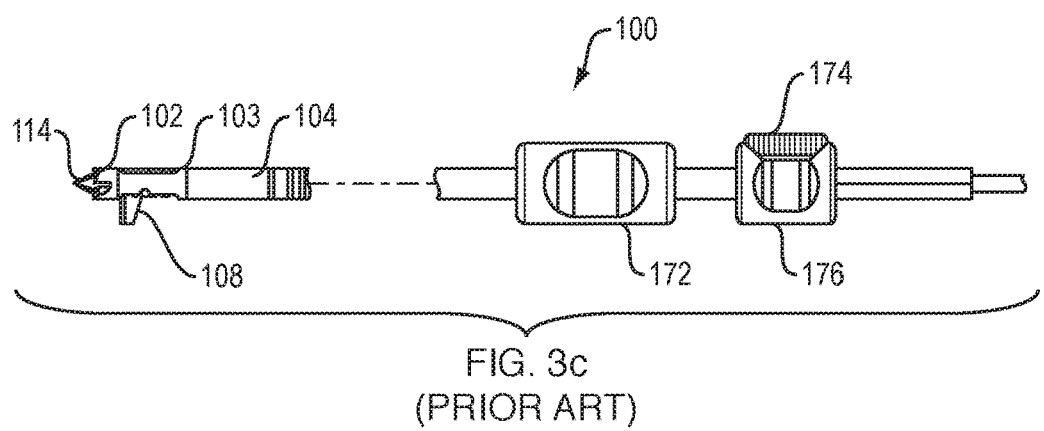

FIGS. 3a-3c depict the deployment of the retro guidewire reamer 100 of FIGS. 1a-2c. As shown in FIG. 3a, the shaft 103 is configured to be disposed over the guidewire 114. As shown in FIG. 3b, once the guidewire 114 is at least partially retracted within the shaft 103, the slide actuator 172 can be moved along the shaft 103 toward the distal end of the shaft 103 in a single manual motion to move the cutting member 108 to its deployed position. As shown in FIG. 3c, once the cutting member 108 is in its fully-deployed position, the lock knob 174 can be rotated to secure, stabilize, and strengthen the guidewire 114, the shaft 103, and the cutting member 108 as a unit. To move the cutting member 108 from its opened or deployed position back to its closed position, the surgeon can move the slide actuator 172 along the shaft 103 toward the proximal end of the shaft 103, thereby closing the cutting member 108. However, attempts by the user to move the slide actuator 172 while the guidewire 114 is still engaged with the cutting member 108 causes the actuator wire 130 to decouple from the slide actuator 172, potentially damaging the mechanical joint between the two.

Having described the above example of a retro guidewire reamer 100, it should be noted that the retro guidewire reamers of this disclosure can take the form of any retro guidewire reamer in which a mechanical joint exists between the actuator wire 130 and the slide actuator 172. Non-limiting examples of suitable retro guidewire reamers are further described in U.S. Publication No. 2014/0276844 to Smith & Nephew, Inc. (Memphis, Tenn.), incorporated herein by reference.

Figure 4A:
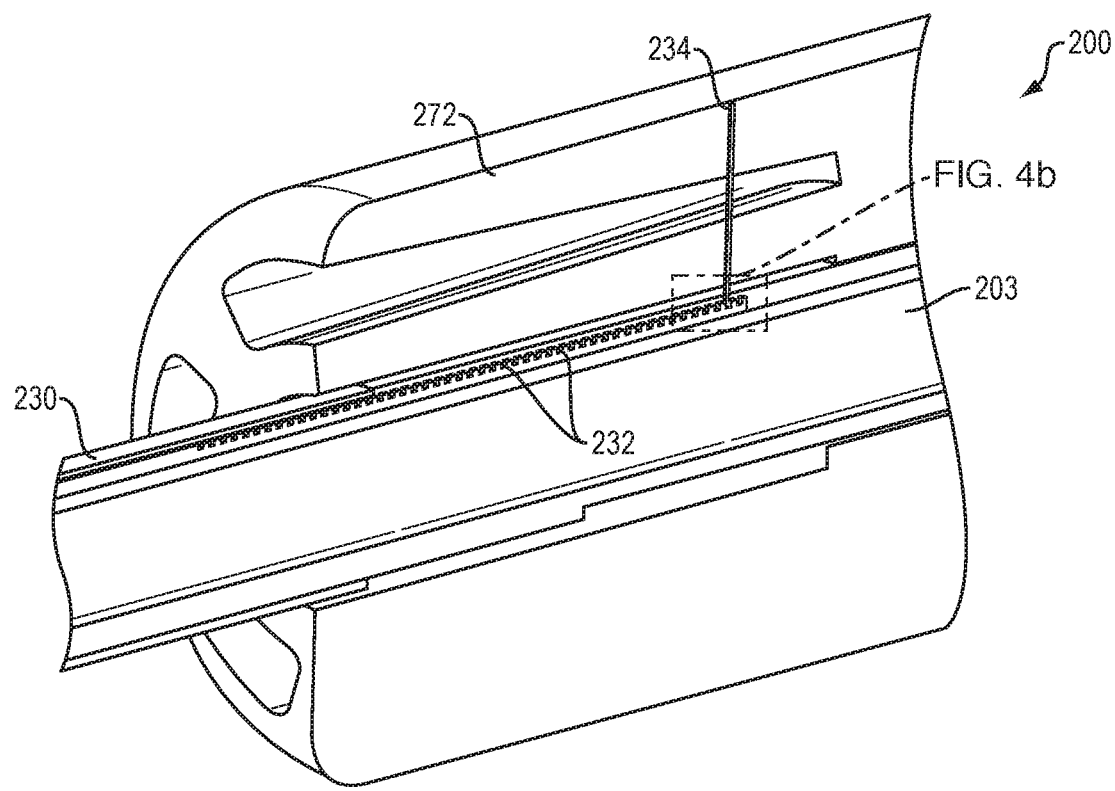
FIGS. 4a and 4b depict a first example of a retro guidewire reamer of this disclosure in a detailed, cross-sectional view.
Figure 4B:
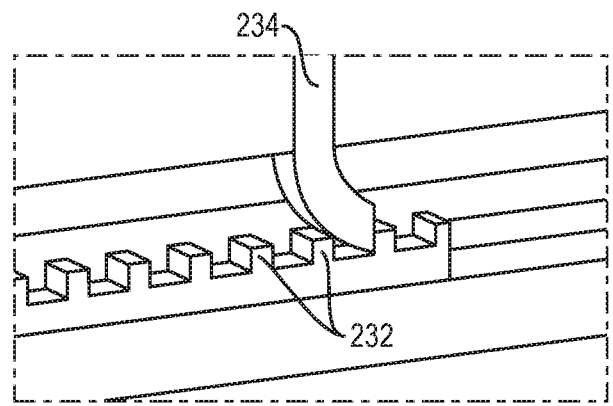

Turning now to FIGS. 4a and 4b, an example of the retro guidewire reamer 200 of this disclosure is shown in a detailed, cross-sectional view. The retro guidewire reamer 200 is substantially similar to the retro guidewire reamer 100 shown in FIGS. 1a-3c, except as described below. As stated above, the retro guidewire reamer 200 provides a mechanism to protect the joint between the actuator wire 230 and the slide actuator 272 when the cutting member (not shown) is obstructed by a guidewire by allowing limited movement of the slide actuator 272 along the drill shaft 203 before the actuator wire 230 is forced to decouple from the slide actuator 272. Specifically, as shown in FIGS. 4a and 4b, the retro guidewire reamer 200 includes a drill having a shaft 203 configured to be disposed over a guidewire, and a slide actuator 272 moveably coupled to the shaft 203. A proximal end of the actuator wire 230 comprises a plurality of teeth 232 configured to engage the tip of a flexible member 234 extending from the slide actuator 272 toward the teeth 232. The plurality of teeth 232 can be formed integrally with the actuator wire 230 in one piece, or can be formed separately as a plastic mold and bonded to the metal actuator wire 230. The tip of the flexible member 234 can be straight, as shown in FIG. 4a, or can be angled to allow for easier motion in one direction than another, as shown in FIG. 4b. The flexible member 234 can comprise a flexible material, such as spring steel or a flexible plastic.

Figure 4C:
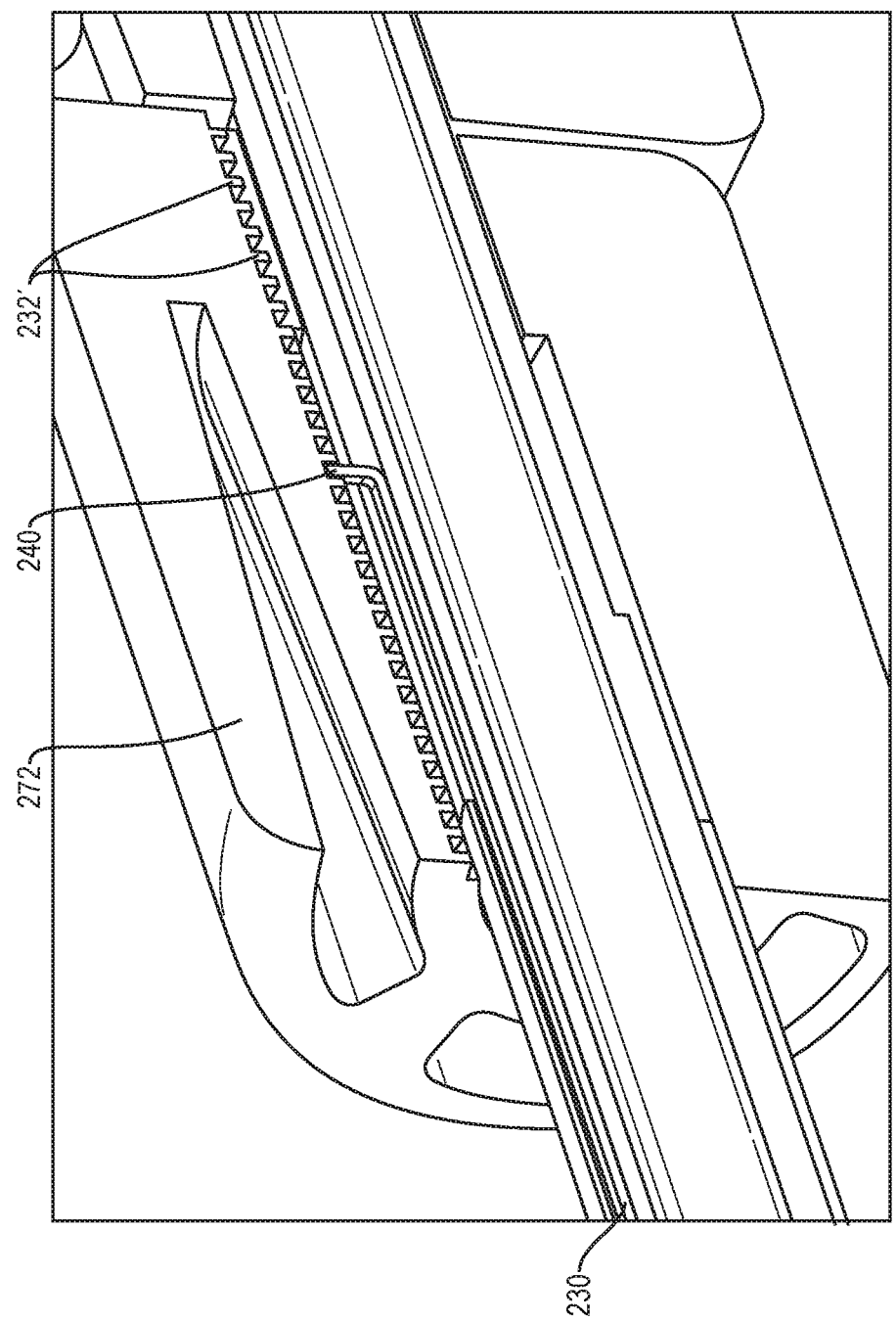
FIG. 4c depicts and alternative embodiment of the retro guidewire reamer of FIGS. 4a and 4b.

The retro guidewire reamer 200 is configured to allow for movement of the slide actuator 272 relative to the shaft 203 at a preselected force when the actuator wire 230 is prevented from sliding along the shaft 203, e.g., when the cutting member is obstructed by the guidewire. In examples where the normal operation force to actuate the cutting member is less than 1 lbf, the mechanism will allow actuation of the cutting member up to this force threshold. In further examples, the force that decouples the actuator wire 230 from the slide actuator 272 is between about 4-8 lbf. The retro guidewire reamer 200 is therefore designed such that the approximate force to decouple the flexible member 234 from the teeth 232 of the actuator wire 230 is above 1 lbf and below 4-8 lbf, allowing the cutting member to be actuated within its design window. It is contemplated by this disclosure that the mechanism could be combined with a spring (not shown) such that the flexible member 234 could ratchet and then be forced back into its original position by the spring. In an alternative example, shown in FIG. 4c, the projection 240 of the actuator wire 230 could be designed to take the place of the flexible member 234, with the teeth 232' molded into the slide actuator 272.

Figure 5A:
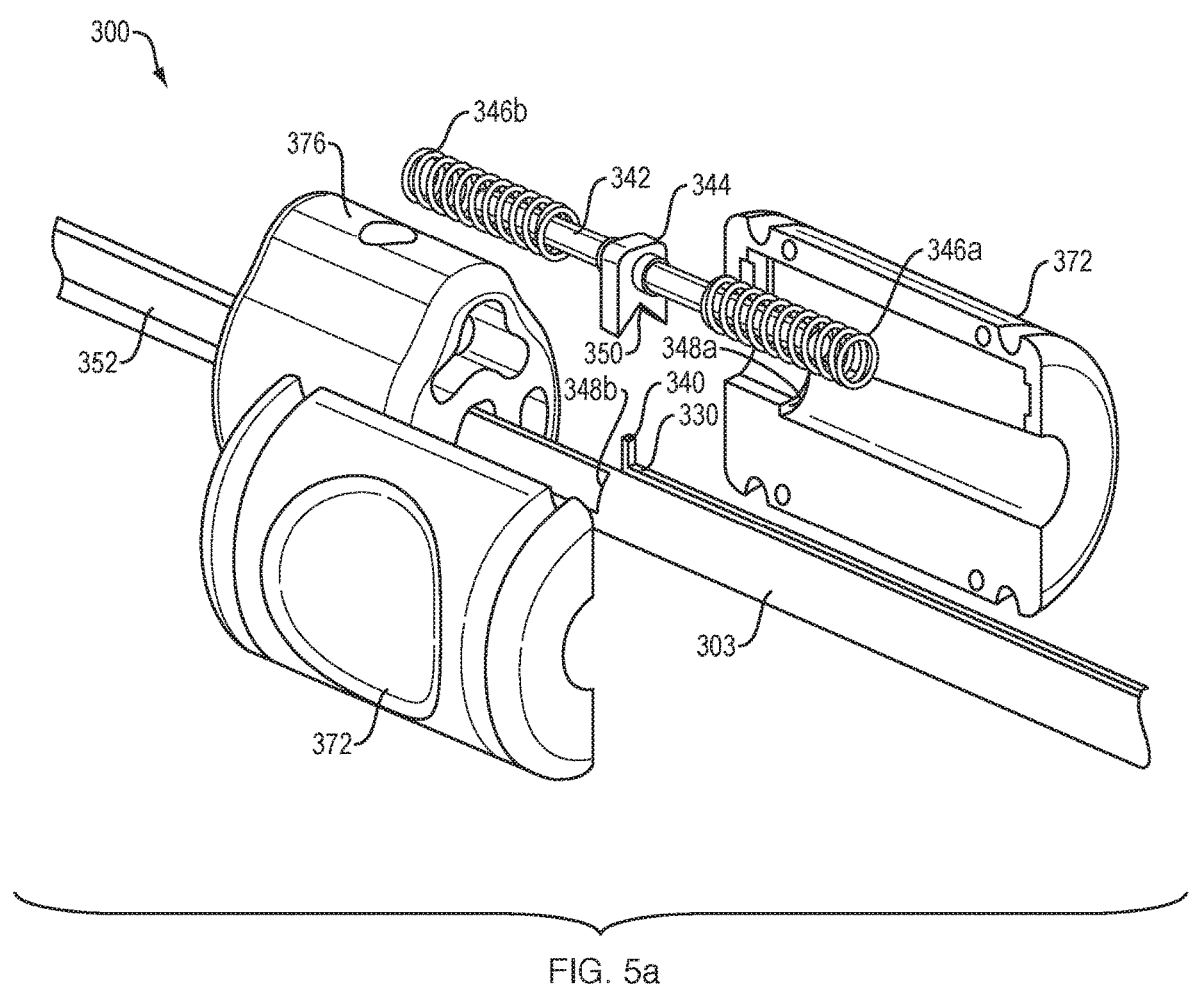
FIG. 5a depicts another example of a retro guidewire reamer of this disclosure in an exploded view.

Turning now to FIG. 5a, an alternative example of the retro guidewire reamer 300 of this disclosure is shown in an exploded view. The retro guidewire reamer 300 is substantially similar to the retro guidewire reamer 100 shown in FIGS. 1a-3c, except as described below. As shown in FIG. 5a, the retro guidewire reamer 300 includes drill having a shaft 303 configured to be disposed over a guidewire. An actuator wire 330 is slidable along the shaft 303, having a projection 340 disposed within a slide actuator 372. The retro guidewire reamer 300 further includes a spring mechanism including a rod 342 fixedly disposed within the slide actuator 372, and a shuttle member 344 configured to move along the rod 342. Two compressions springs 346a, 346b are disposed on the rod 342 on opposite sides of the shuttle member 344. The shuttle member 344 contains a slot 350 to receive the projection 340 of the actuator wire 330. In examples, proximal motion of the slide actuator 372 relative to the shaft 303 is limited by the plunger support 376, while distal motion is restricted by a stop surface 348a on an internal bore of the slide actuator 372 and a corresponding stop surface 348b on the shaft 303. Under normal use conditions (i.e., the cutting member is unobstructed by the guidewire), the spring force of the compression springs 346a, 346b exceeds the normal operation force needed to deploy the cutting member (e.g., less than 1 lbf). Therefore, the compression springs 346a, 346b would not be compressed by the shuttle member 344 under normal use conditions. However, in the event that the cutting member is obstructed by the guidewire, the force applied by the user to the slide actuator 372 would cause the shuttle member 344 to compress one of the compression springs 346a, 346b prior to generating forces sufficient to compromise the joint strength between the shuttle member 344 and the actuator wire 330.

Figure 5B:
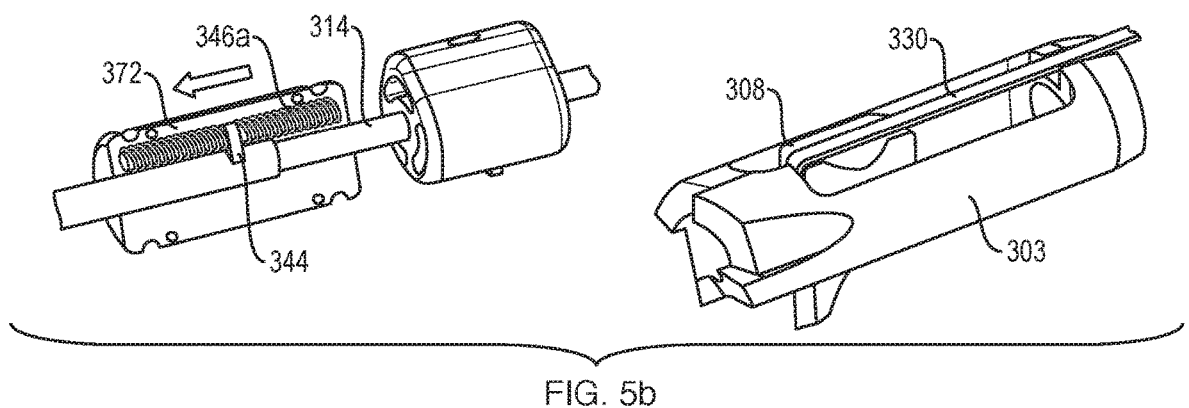
Figure 5C:
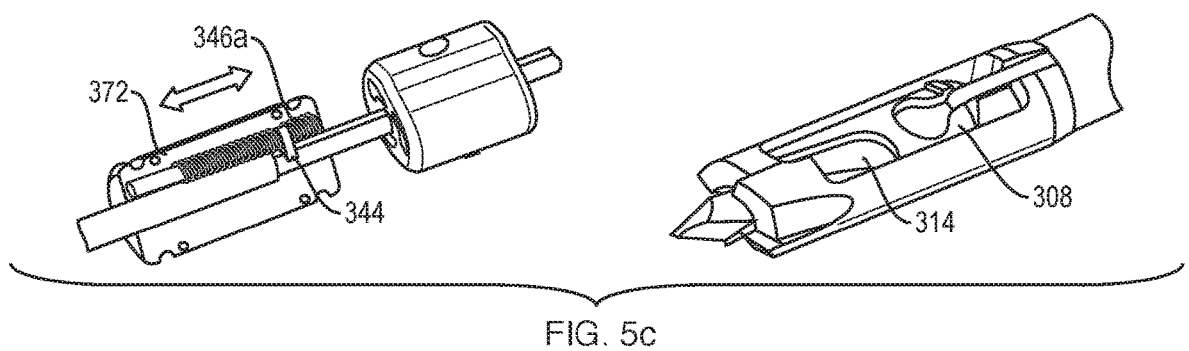
Figure 5D:
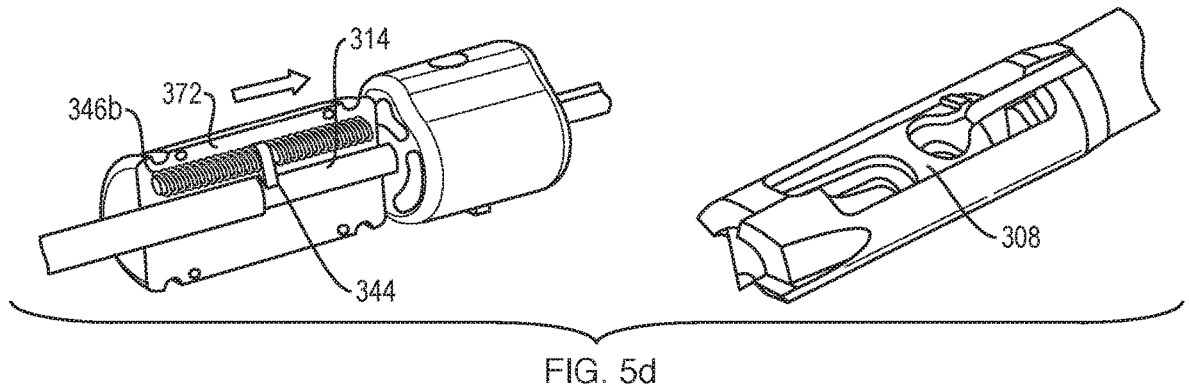
Figure 5E:
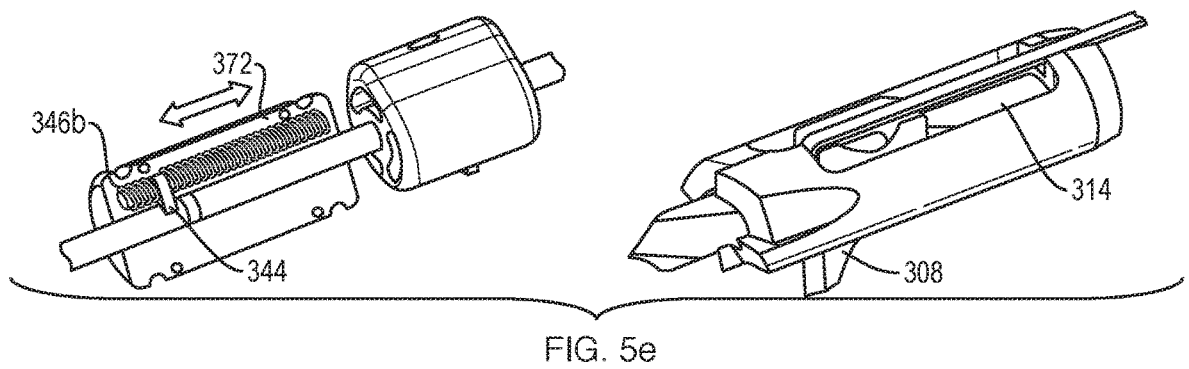

Specifically, as shown in more detail in FIG. 5b, under normal use conditions (i.e., the cutting member 308 is not obstructed by the guidewire 314), the user moves the slide actuator 372 distally to deploy the cutting member 308 to its retrograde position. In this scenario, the compression spring 346a is not compressed by the shuttle member 344. However, as shown in FIG. 5c, when the cutting member 308 is obstructed by the guidewire 314 and the user attempts to move the slide actuator 372 distally to deploy the cutting member 308, the compression spring 346a is compressed by the shuttle member 344 and exerts a counterforce on the shuttle member 344, causing the slide actuator 372 to spring back to its original position. Ideally, the user would see that motion of the slide actuator 372 does not result in deployment of the cutting member 308 and would recognize that the guidewire 314 is obstructing the motion of the cutting member 308. Similarly, as shown in FIG. 5d, under normal use conditions, the user moves the slide actuator 372 proximally to retract the cutting member 308 to its closed position. In this scenario, the compression spring 346b is not compressed by the shuttle member 344. However, as shown in FIG. 5e, when the cutting member 308 is obstructed by the guidewire 314 and the user attempts to move the slide actuator 372 proximally to retract the cutting member 308, the compression spring 346b is compressed by the shuttle member 344 and exerts a counterforce on the shuttle member 344.

It should be noted that, while two compression springs 346a, 346b are shown in FIGS. 5a-e, a single-spring alternative would suit those applications that only require single-direction protection of the mechanical joint between the slide actuator 372 and the actuator wire 330. It is further contemplated by this disclosure that the compression springs 346a, 346b could be substitute with alternative spring types. In other examples, not shown, it is contemplated that the shuttle member 344 is rigidly fixed to the actuator wire 330 by means such as over-molding a plastic shuttle member 344 to the metal actuator wire 330. Finally, it is contemplated that the actuator wire 330 could be coupled to the slide actuator 372 via a compliant flexure (not shown), thus eliminating the need for the compression springs 346.

It should also be noted that, while the mechanisms described above with regard to FIGS. 4a-5e relate to the protection of a mechanical joint between an actuator wire and a slide actuator of a retro guidewire reamer, the mechanisms could also be configured for use in any type of linear motion device that requires a force limiter. Furthermore, the mechanisms described above with regard to FIGS. 4a-5e are designed to protect the mechanical joint between the actuator wire and the slide actuator by allowing for limited movement of the slide actuator relative to the shaft when the cutting member is obstructed by the guidewire. Other mechanisms, described in more detail below, provide protection to the mechanical joint by preventing movement of the slide actuator relative to the shaft when the cutting member is obstructed by the guidewire.

Figure 6A:
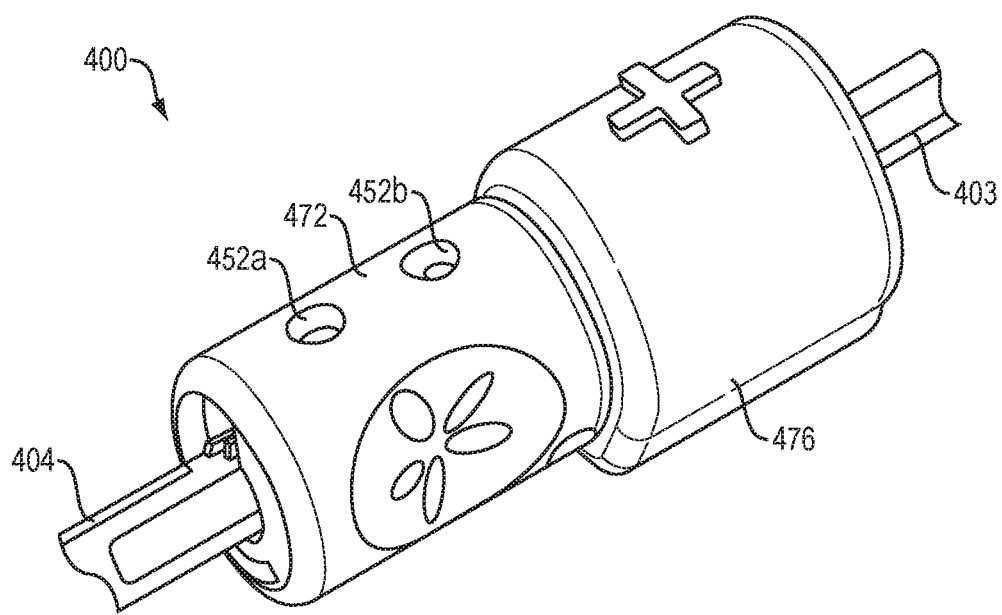
FIGS. 6a and 6b depict another example of a retro guidewire reamer of this disclosure in a detailed, perspective view.
Figure 6B:
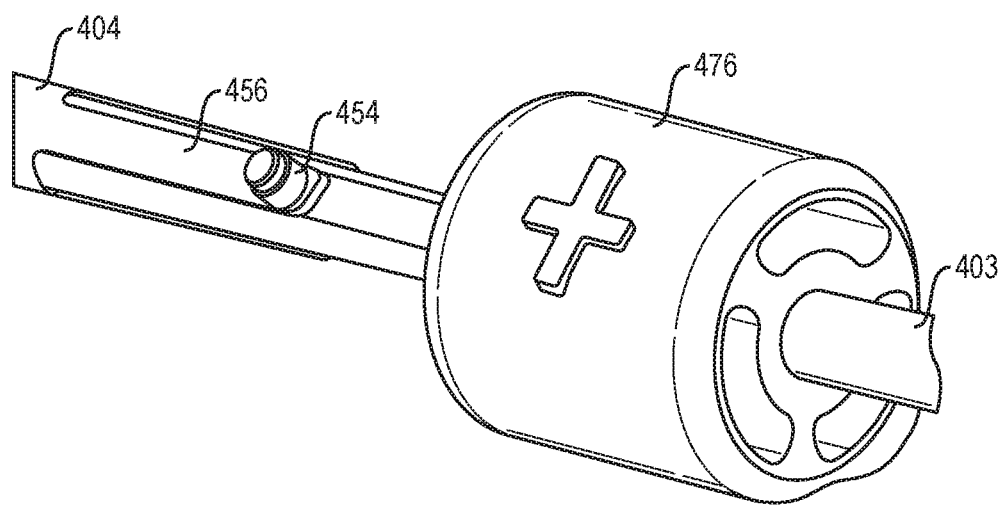

Turning now to FIG. 6a, an alternative example of the retro guidewire reamer 400 of this disclosure is shown in a detailed, perspective view. The retro guidewire reamer 400 is substantially similar to the retro guidewire reamer 100 shown in FIGS. 1a-3c, except as described below. As shown in FIG. 6a, the retro guidewire reamer 400 includes drill having a shaft 403 configured to be disposed over a guidewire, a sheath 404, a slide actuator 472, and a plunger support 476. As further shown in FIG. 6a, the slide actuator 472 comprises a distal hole 452a and a proximal hole 452b, as described in more detail below. As shown in FIG. 6b, the sheath 404 has a spring element 456, such as a beam spring, that extends proximally toward the plunger support 476. A lock pin 454 is fixed to the spring element 456 of the sheath 404. The sheath 404 is coaxial with the shaft 403 and its position is fixed relative to the shaft 403.

Figure 6C:
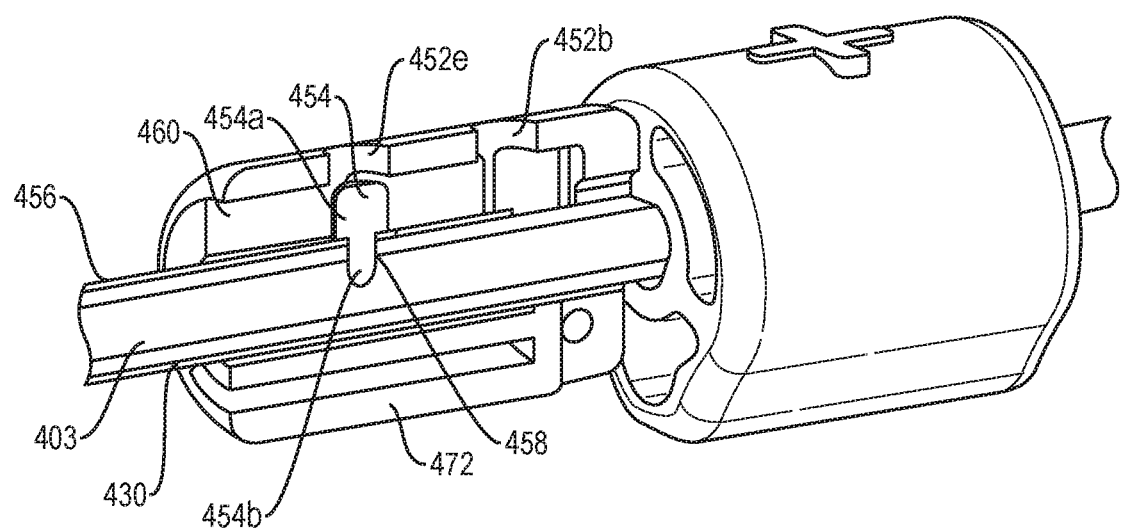
FIGS. 6c-e illustrate the use of the retro guidewire reamer of FIGS. 6a and 6b.
Figure 6D:
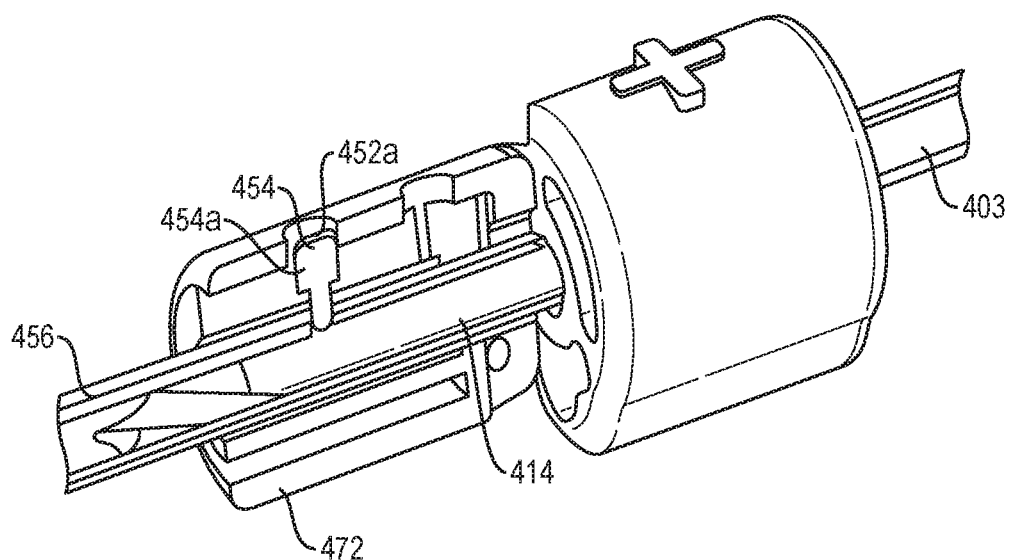
Figure 6E:
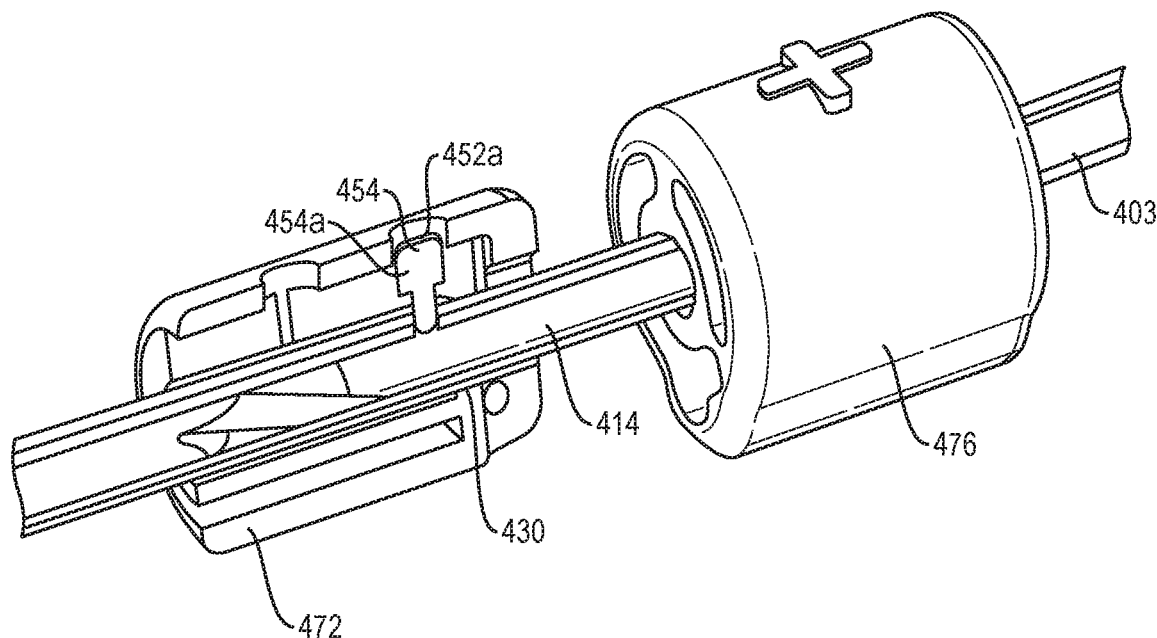

As shown in FIG. 6c, the lock pin 454 includes an outer portion 454a projecting radially from the spring element 456 and an inner portion 454b extending through the spring element 456 and through a transverse hole 458 in the shaft 403 in communication with the interior of the shaft 403. The distal and proximal holes 452a, 452b in the slide actuator 472 align with the transverse hole 458 in the shaft 403 when the slide actuator 472 is positioned in either the retrograde or antegrade position, respectively. While the distal and proximal holes 452a, 452b are shown in FIG. 6c as circular holes, slots or tapered holes are also contemplated by this disclosure. Furthermore, the holes 452a, 452b are not limited to through holes, depending on method of manufacture. A diameter of the outer portion 454a of the lock pin 454 is selected to be greater than a diameter of the inner portion 454b of the lock pin 454. Furthermore, a size of the distal and proximal holes 452a, 452b, as well as a size of an interior slot 460 of the slide actuator 472, are selected to provide a clearance fit with the outer portion 454a of the lock pin 454. Under normal use conditions (i.e., when the cutting member is not obstructed by the guidewire), radial clearance between the top surface of the lock pin 454 and the upper surface of the interior slot 460 allows the slide actuator 472 to move freely over the outer portion 454a of the lock pin 454 to deploy and retract the cutting member. However, as shown in FIG. 6d, when the guidewire 414 is present in the shaft 403 and the slide actuator 472 is in the antegrade position, the guidewire 414 causes the lock pin 454 to be displaced radially by flexing of the spring element 456, the spring element 456 controlling the displacement path of the lock pin 454. When the lock pin 454 is displaced, the outer portion 454a engages with the distal hole 452a of the slide actuator 472, thus locking the slide actuator 472 in the antegrade position. Similarly, as shown in FIG. 6e, when the guidewire 414 is present in the shaft 403 and the slide actuator 472 is in the retrograde position, the outer portion 454a of the lock pin 454 engages with the proximal hole 452b of the slide actuator 472, locking the slide actuator 472 in the retrograde position. Such impeded movement of the slide actuator 472 will cause the user to recognize that the guidewire 414 is obstructing motion of the cutting member and will retract the guidewire 414.

Figure 6F:
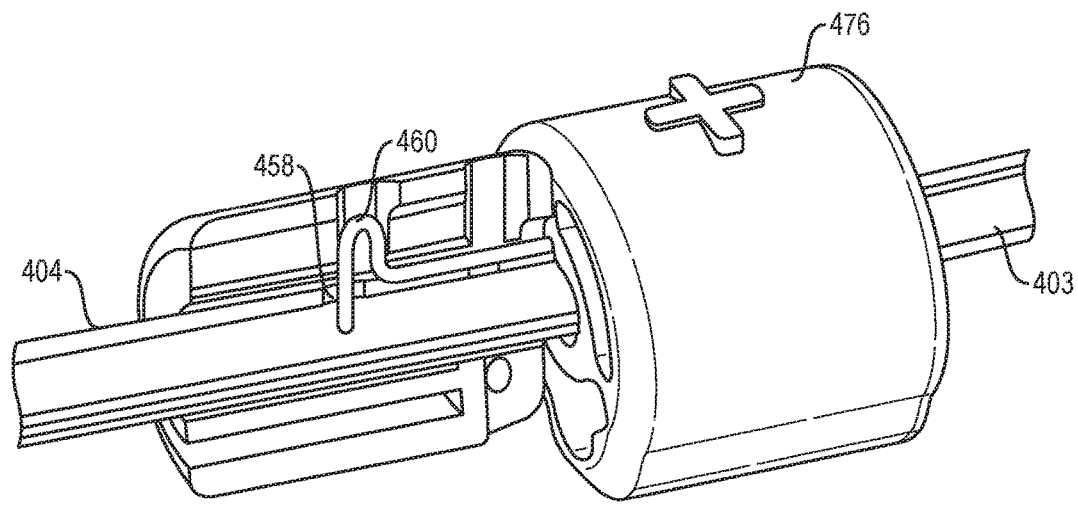
FIGS. 6f-i depict alternative embodiments of the retro guidewire reamer of FIGS. 6a and 6b.
Figure 6G:
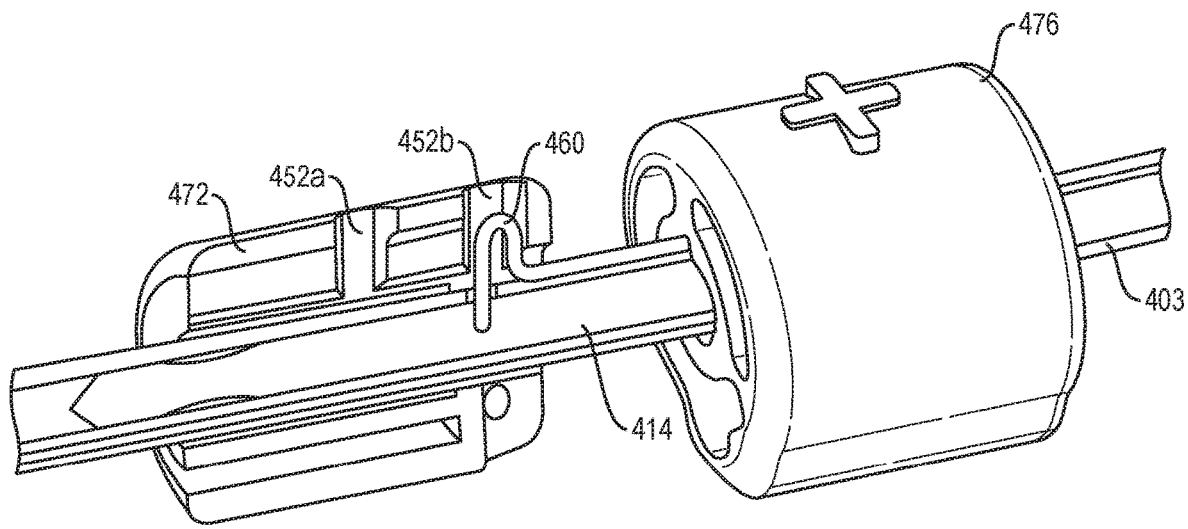
Figure 6H:
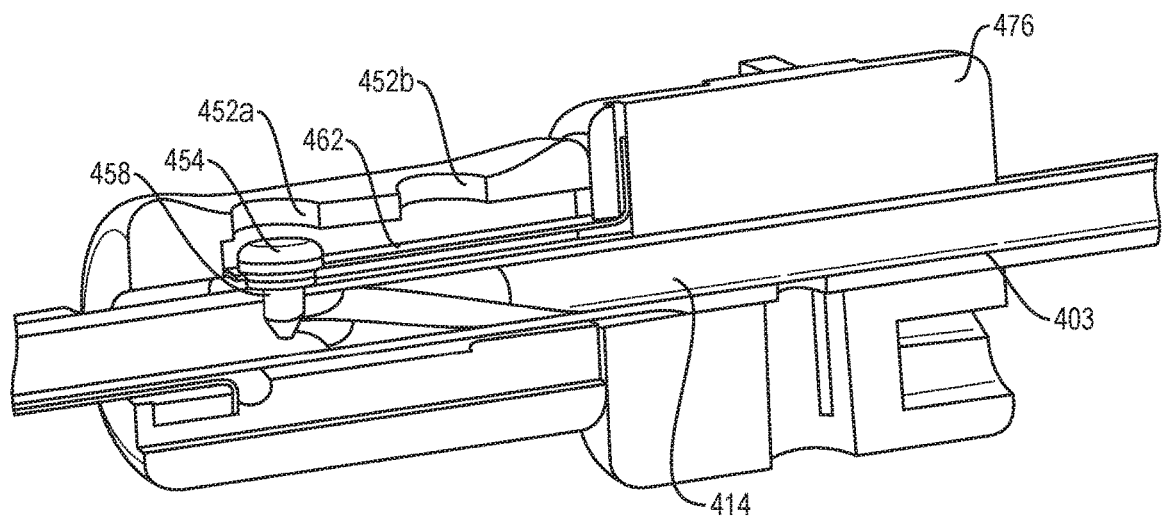
Figure 6I:
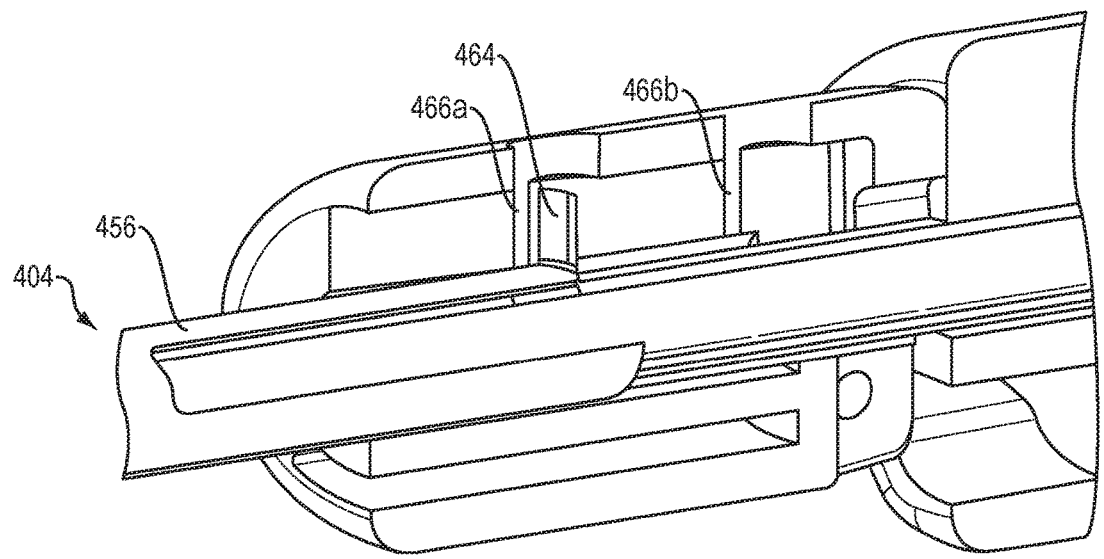

In an alternative example, shown in FIG. 6f, the spring element 456 of the sheath 404 and the lock pin 454 could be replaced with a formed spring 460. The formed spring 460 is fixed at one end to the plunger support 476 and aligned with the transverse hole 458 in the shaft 403 to provide for communication with the interior of the shaft 403. When a guidewire 414 is present in the shaft 403 (FIG. 6g), the spring 460 would deflect, causing the top bend of the spring 460 to engage with one of the proximal and distal holes 452a, 452b in the slide actuator 472. Alternatively, the spring element 456 of the sheath 404 could be replaced with a separate spring component 462 fixed to the plunger support 476, as shown in FIG. 6h. The spring component 462 extends distally from the plunger support 476 such that the attached lock pin 454 is aligned with the transverse hole 458 in the shaft 403, allowing for communication of the lock pin 454 with the guidewire 414. The guidewire 414 radially displaces the lock pin 454, causing the lock pin 454 to engage with one of the distal and proximal holes 452a, 452b in the slide actuator 472. In yet another example, the lock pin 454 could be omitted in lieu of an additional bend or tab 464 formed at the proximal end of the spring element 456 of the sheath 404, as shown in FIG. 6i. The tab 464 would engage with a mating slot 466a, 466b in the slide actuator 472. In this example, the slot 466 in the slide actuator 472 could be round or could have an oval shape to more closely approximate the geometry of the tab 464.

In further examples, not shown, it is contemplated by this disclosure that the spring element 456 of the sheath 404 could include alternative spring geometries. For example, the spring element 456 could be constructed to minimize flexure, with the lock pin 454 slidingly engaging a hole in the spring element 456. The hole in the spring element 456 would act as a bushing, whereby the lock pin 454 would float radially until a guidewire 414 was present in the shaft 403, forcing the lock pin 454 radially outward to engage one of the distal and proximal holes 452a, 452b in the slide actuator 472.

Figure 7A:
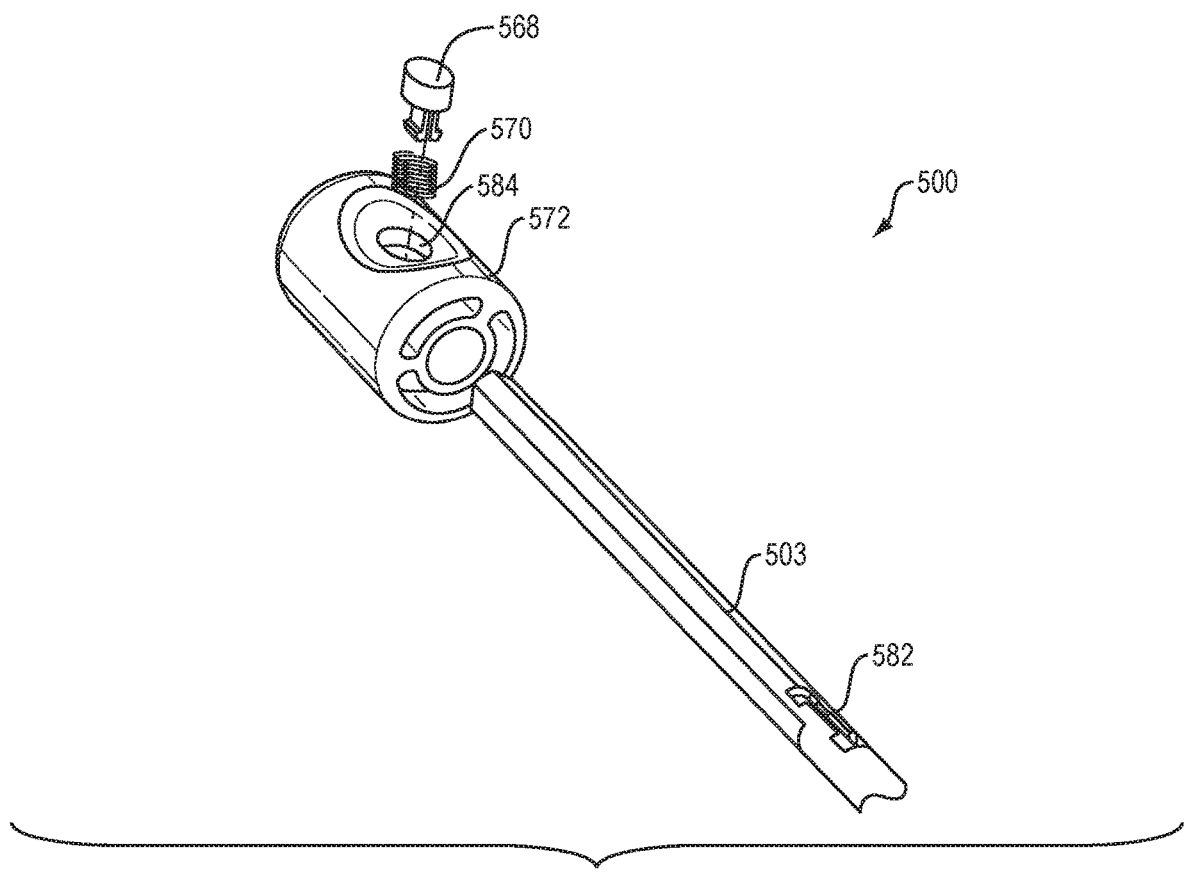
FIGS. 7a and 7b depict another example of a retro guidewire reamer of this disclosure in an exploded view (FIG. 7a) and an assembled view (FIG. 7b)
Figure 7B:
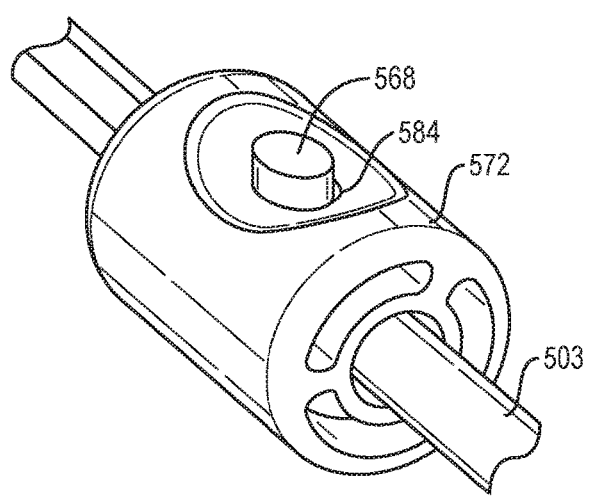

Turning now to FIGS. 7a and 7b, an alternative example of the retro guidewire reamer 500 of this disclosure is shown in an exploded view (FIG. 7a) and an assembled view (FIG. 7b). The retro guidewire reamer 500 is substantially similar to the retro guidewire reamer 100 shown in FIGS. 1a-3c, except as described below. As shown in FIGS. 7a and 7b, the retro guidewire reamer 500 includes a drill having a shaft 503, a slide actuator 572, a pushbutton 568 and a spring 570, as further described below. The slide actuator 572 includes an opening 584 in communication with an interior of the slide actuator 572. A cut-out or slot 582 extends through a surface of the shaft 503 in communication with the interior of the shaft 503.

Figure 7C:
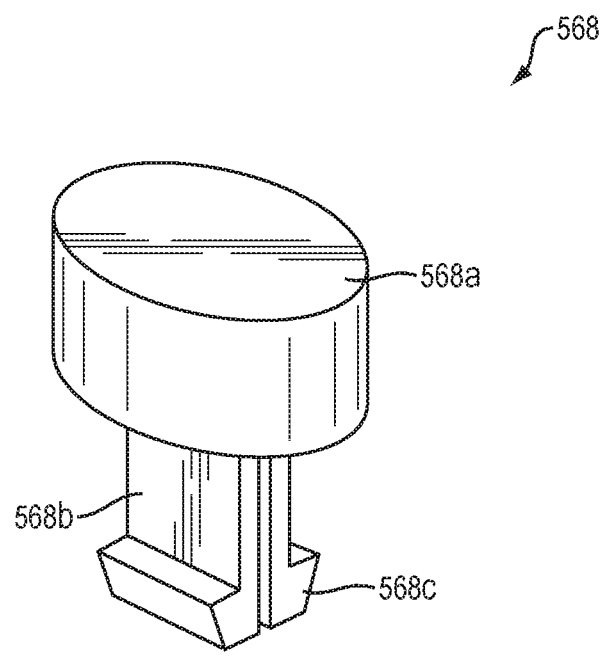
FIGS. 7c and 7d are detailed views of components of the retro guidewire reamer of FIGS. 7a and 7b.
Figure 7D:
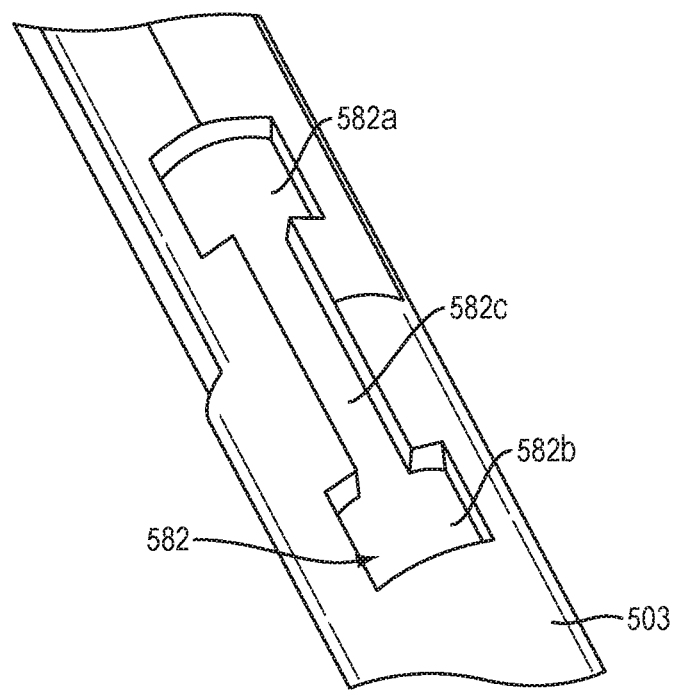

As shown in more detail in FIG. 7c, the pushbutton 568 includes an outer portion 568a and an inner portion 568b terminating in a foot portion 568c. A diameter of the foot portion 568c is selected to be wider than a diameter of the inner portion 568b. As further shown in FIG. 7d, the slot 582 in the shaft 503 has an "I" shape, such that a diameter of a proximal region 582a and a distal region 582b of the slot 582 is selected to be wider than a diameter of an intermediate region 582c of the slot 582. In particular, the diameter of the proximal and distal regions 582a, 582b of the slot 582 are selected to accommodate the foot portion 568c of the pushbutton 568, while the diameter of the intermediate region 582c of the slot 582 is selected to accommodate the inner portion 568b of the pushbutton 568, while prohibiting travel of the foot portion 568c along the slot 582, as further described below. The proximal region 582a and the distal region 582b of the slot 582 correspond to the retracted and deployed positions of the cutting member, respectively.

Figure 7E:
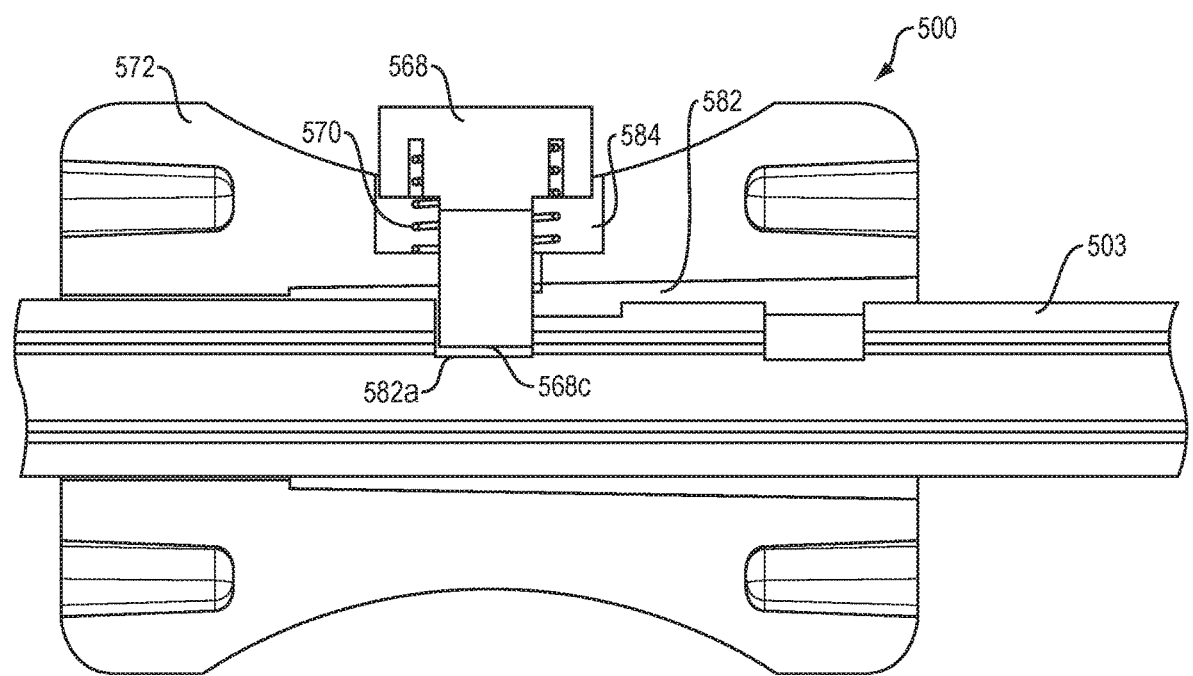
FIGS. 7e-h illustrate the use of the retro guidewire reamer of FIGS. 7a and 7b.
Figure 7F:
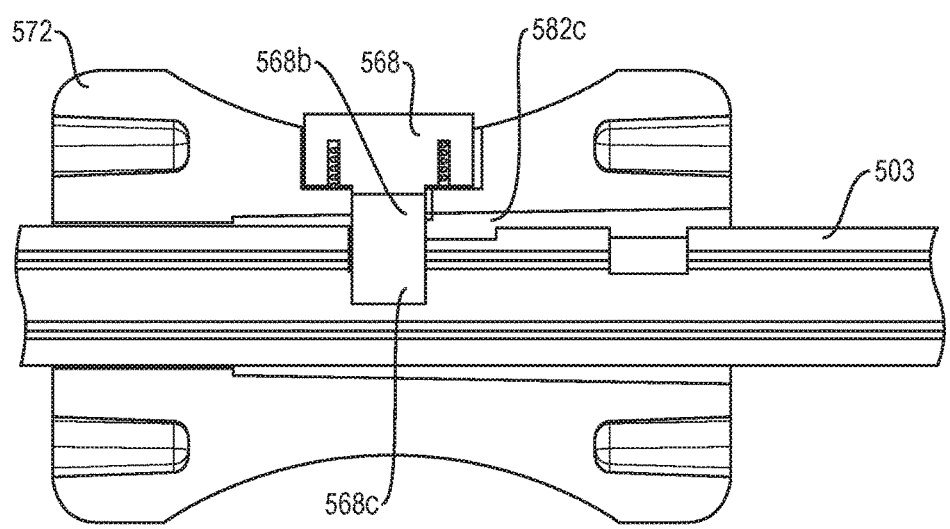
Figure 7G:
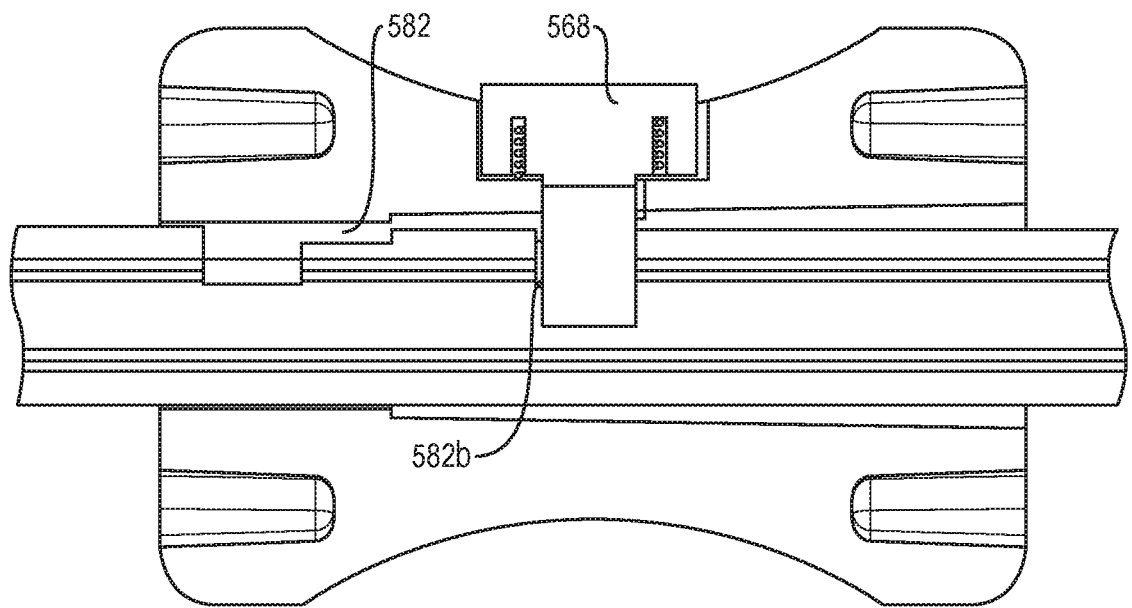
Figure 7H:
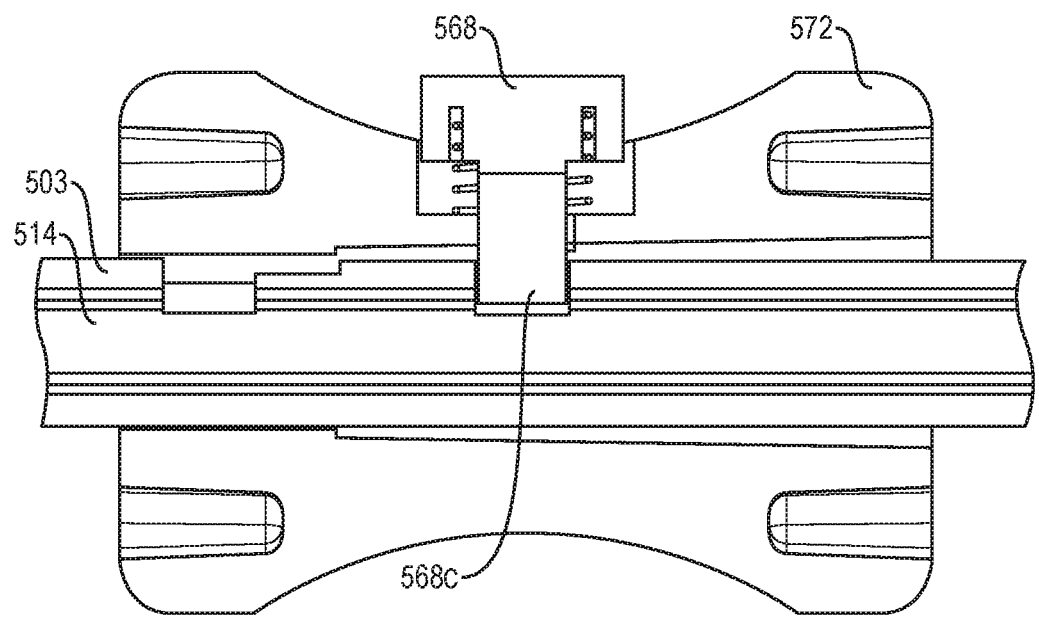

Turning now to FIG. 7e, a cross-sectional view of the retro guidewire reamer 500 is shown. The spring 570 is disposed within the opening 584 of the slide actuator 572 and the pushbutton 568 is snap-fitted over the spring 570 while the slide actuator 572 is aligned with the slot 582. Alternatively, the pushbutton 568 could be incorporated into the slide actuator 572 in a one-piece design. In FIG. 7e, the slide actuator 572 is shown in the antegrade position and the pushbutton 568 is at rest such that the foot portion 568c of the pushbutton 568 is disposed within the proximal region 582a of the slot 582. The pushbutton 568 is in a raised position due to the force of the spring 570 such that the foot portion 568c does not protrude into the interior of the shaft 503. To advance the slide actuator 572 to the retrograde position, the user holds down the pushbutton 568, as illustrated in FIG. 7f. Where no guidewire is present within the shaft 503, the pushbutton 568 allows for movement of the slide actuator 572 as the foot portion 568c of the pushbutton 568 enters the shaft 503 and the inner portion 568b of the pushbutton 568 is slidable along the intermediate region 582c of the slot 582 until the pushbutton 568 is aligned with the distal region 582b of the slot 582 (FIG. 7g). However, when a guidewire 514 is present within the shaft 503 (FIG. 7h), the interference between the foot portion 568c of the pushbutton 568 and the guidewire 514 will prevent the foot portion 568c of the pushbutton 568 from entering the shaft 503, thus preventing movement of the slide actuator 572.

As stated above, the mechanisms described with regard to FIGS. 4a-7h relate to the protection of a mechanical joint between an actuator wire and a slide actuator of a retro guidewire reamer when the cutting member is obstructed by the guidewire. In the retro guide wire reamers described above, the guidewire is necessary to support the cutting member in place during retrograde drilling, since deploying the cutting member requires flipping the cutting member towards the user, leaving the cutting member unsupported by the surrounding structures. Other mechanisms, described in more detail below, provide protection to the mechanical joint by allowing the cutting member to deploy away from the user such that the cutting member is supported by the surrounding regions of the shaft. In such examples, a guidewire would not required for use of the device.

Figure 8A:
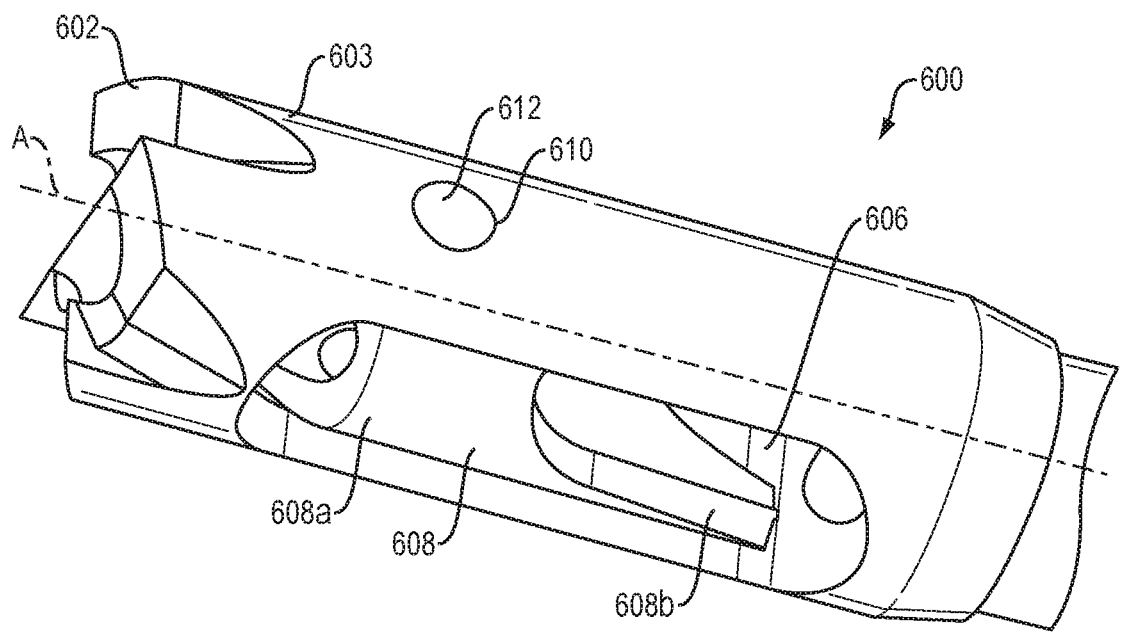
FIGS. 8a-c depict another example of a retro guidewire reamer of this disclosure.

Turning now to FIG. 8a, an alternative example of the retro guidewire reamer 600 of this disclosure is shown in a detailed, perspective view. The retro guidewire reamer 600 is substantially similar to the retro guidewire reamer 100 shown in FIGS. 1a-3c, except as described below. As shown in FIG. 8a, the retro guidewire reamer 600 includes a drill having a shaft 603, the distal end of the shaft 603 defining a drilling bit 602. The cutting member 608 is disposed within a cavity 606 formed adjacent the distal end of the shaft 603. The cavity 606 comprises holes 610 for pins 612 on opposite sides of the shaft 603 to keep the cutting member 608 in place. In its closed position, the cutting member 608 has a first end 608a pivotally attached to the shaft 603 at a distal end of the cavity 606 and a second end 608b defining a cutting end disposed within a proximal end of the cavity 606. The cutting member 608 is pivotable about an axis of rotation that is perpendicular to a longitudinal axis A of the shaft 603.

Figure 8B:
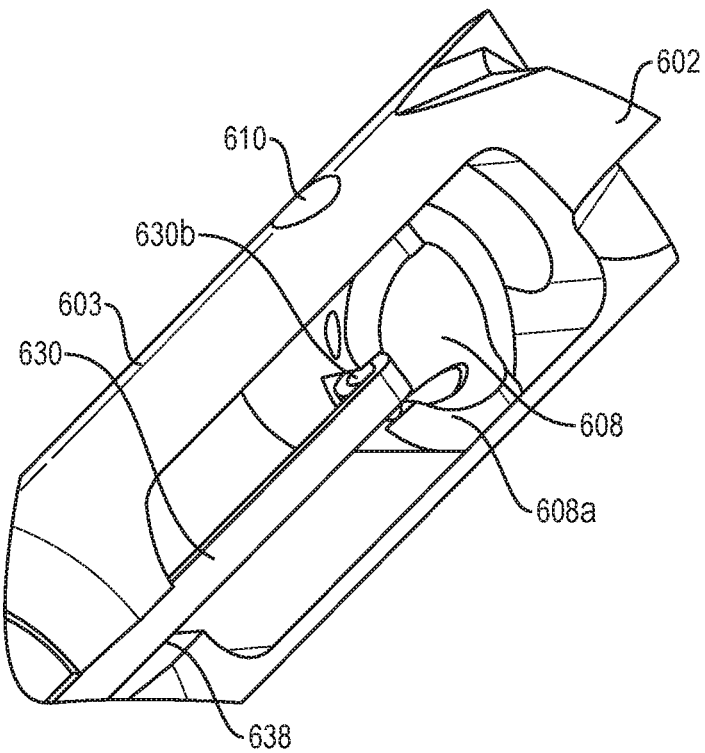
Figure 8C:
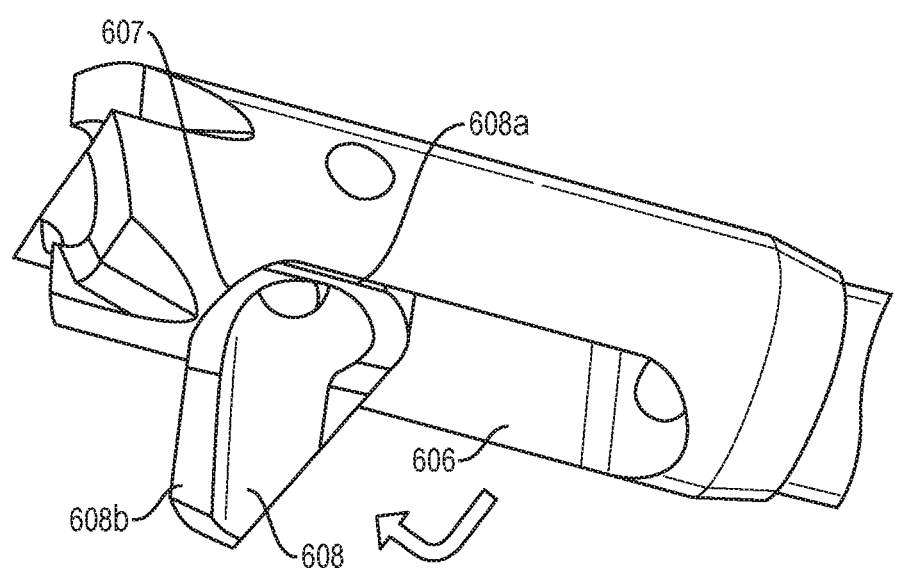

As shown in FIG. 8b, the actuator wire 630 extends along a slot 638 in the shaft 603 with a distal end 630b of the actuator wire 630 being operatively coupled to the first end 608a of the cutting member 608. A slide actuator (not shown) is operatively coupled to the proximal end of the actuator wire 630 such that longitudinal movement of the slide actuator along the shaft 603 is effective to pivot the cutting member about the axis of rotation between a retracted position, in which the second end 608b does not protrude from the cavity 606 (FIG. 8a), and a deployed position, in which the second end 608b protrudes from the cavity 606 (FIG. 8c). As such, the cutting member 608 flips in a deployment direction away from the user such that the deployed position of the second end 608b of the cutting member 608 is distal to the retracted position of the second end 608b. Once deployed, the first end 608a of the cutting member 608 rests against a distal wall 607 of the cavity 606, providing sufficient resistance to the cutting member 608 so that the cutting member 608 can be used to form the counterbore without a guidewire in place.

While the disclosure has been particularly shown and described with references to preferred examples thereof, it will be understood by those skilled in the art that various changes in form and details may be made therein without departing from the spirit and scope of the present application as defined by the appended claims. Such variations are intended to be covered by the scope of this present application. As such, the foregoing description of examples of the present application is not intended to be limiting, the full scope rather being conveyed by the appended claims.

What is claimed is:

1. A surgical instrument comprising:
 a tubular shaft having a distal end and a proximal end, the shaft configured to be disposed over a guidewire;
 at least one cutting member movably disposed adjacent the distal end of the shaft;
 a slide actuator moveably coupled to the shaft; and
 an actuator wire slidable along the shaft, the actuator wire having a first end coupled to the slide actuator and a second end coupled to the at least one cutting member, the actuator wire operative to move the at least one cutting member between a closed position and a deployed position when the slide actuator is moved along the shaft;
 wherein one of the actuator wire and the slide actuator comprises a plurality of teeth configured to engage a flexible member extending from the other of the actuator wire and the slide actuator; and
 wherein the flexible member is configured to allow for movement of the slide actuator relative to the shaft at a preselected force when the actuator wire is prevented from sliding along the shaft.

2. The surgical instrument of claim 1, wherein the preselected force is between about 1 lbf and about 8 lbf.

3. The surgical instrument of claim 1, wherein the plurality of teeth are formed integrally with the one of the actuator wire and the slide actuator.

4. The surgical instrument of claim 1, wherein the plurality of teeth are formed separately and bonded to the one of the actuator wire and the slide actuator.

5. A surgical instrument comprising:
 a tubular shaft having a distal end and a proximal end, the shaft configured to be disposed over a guidewire;
 at least one cutting member movably disposed adjacent the distal end of the shaft;
 a slide actuator moveably coupled to the shaft;
 an actuator wire slidable along the shaft, the actuator wire having a first end disposed within the slide actuator and a second end coupled to the at least one cutting member, the actuator wire operative to move the at least one cutting member between a closed position and a deployed position when the slide actuator is moved along the shaft; and
 a spring mechanism including a rod fixedly disposed within the slide actuator and a shuttle member configured to move along the rod adjacent at least one compression element, the shuttle member coupled to the first end of the actuator wire;
 wherein the shuttle member is configured to compress the at least one compression element, allowing for movement of the slide actuator relative to the shaft when the actuator wire is prevented from sliding along the shaft.

6. The surgical instrument of claim 5, wherein the at least one compression element is two compression elements, and the shuttle member is disposed between the two compression elements.

7. The surgical instrument of claim 5, wherein the at least one compression element is a spring.

8. The surgical instrument of claim 5, wherein the first end of the actuator wire is rigidly coupled to the shuttle member.

9. A surgical instrument comprising:
 a tubular shaft having a cannulation extending from a distal end to a proximal end, the shaft configured to be disposed over a guide wire;
 at least one cutting member moveably disposed adjacent the distal end of the shaft;
 a sheath member axially aligned with the shaft, the sheath member including a pin having an outer portion projecting radially from the sheath member and an inner portion extending through a transverse hole in the shaft in communication with the cannulation;
 a slide actuator moveably coupled to the shaft, the slide actuator operatively coupled to the at least one cutting member for moving the at least one cutting member between a retracted and a deployed position, the slide actuator comprising:
  an internal slot configured to receive the outer portion of the pin such that the outer portion of the pin is slideable within the slot; and
  at least one opening in communication with the slot, the at least one opening configured to receive the outer portion of the pin,
 wherein, when the outer portion of the pin is not engaged with the at least one opening, the slide actuator is moveable relative to the shaft, and when the outer portion is engaged with the at least one opening, the slide actuator is fixed relative to the shaft.

10. The surgical instrument of claim 9, wherein the at least one opening in the slide actuator is two openings, the two openings corresponding to the retracted and deployed position of the cutting member, respectively.

11. The surgical instrument of claim 9, wherein the pin is attached to a spring element of the sheath, the spring element controlling a displacement path of the pin.

12. The surgical instrument of claim 11, wherein the spring element is a beam spring.

13. A surgical instrument comprising:
  a tubular shaft having a cannulation extending from a proximal end to a distal end, at least one cutting member moveably disposed adjacent the distal end of the shaft;
  a slot extending through a surface of the shaft in communication with the cannulation, a diameter of a proximal region and a distal region of the slot selected to be wider than a diameter of an intermediate region of the slot;
  a slide actuator slideably coupled to the shaft, the slide actuator operative to move the at least one cutting member between a retracted and a deployed position, the slide actuator comprising a transverse opening in communication with the slot;
  a pin having an outer portion and an inner portion terminating in a foot portion, a diameter of the foot portion selected to be wider than a diameter of the inner portion, the pin at least partially disposed within the opening of the slide actuator such that the foot portion extends into one of the proximal or distal regions of the slot;
  wherein the pin is actuable from a first position, in which interference between the foot portion of the pin and the intermediate region of the slot prevents the slide actuator from axial movement along the shaft, to a second position, in which the foot portion of the pin extends into the cannulation of the shaft and the slide actuator is axially moveable along the shaft.

14. The surgical instrument of claim 13, further comprising a spring radially disposed about the inner portion of the pin, the spring configured to bias the outer portion of the pin away from the shaft.

15. The surgical instrument of claim 13, wherein the inner portion of the pin is configured to axially slide along the intermediate region of the slot.

16. The surgical instrument of claim 13, wherein the proximal and distal regions of the slot correspond to the retracted and deployed positions of the cutting member, respectively.

* * * * *